US008691776B2

(12) United States Patent
Beck et al.

(10) Patent No.: US 8,691,776 B2
(45) Date of Patent: *Apr. 8, 2014

(54) SYNTHESIS OF HIGH MOLECULAR WEIGHT IRON-SACCHARIDIC COMPLEXES

(75) Inventors: Robert A. Beck, Framingham, MA (US); Robert A. Mateer, Jr., Douglas, MA (US); John Kowalski, Plymouth, MA (US)

(73) Assignee: Chromaceutical Advanced Technologies, Inc., Hopkinton, MA (US)

( * ) Notice: Subject to any disclaimer, the term of this patent is extended or adjusted under 35 U.S.C. 154(b) by 95 days.

This patent is subject to a terminal disclaimer.

(21) Appl. No.: 13/108,392

(22) Filed: May 16, 2011

(65) Prior Publication Data

US 2011/0220539 A1 Sep. 15, 2011

Related U.S. Application Data

(63) Continuation of application No. 10/853,951, filed on May 26, 2004, now Pat. No. 7,964,568.

(60) Provisional application No. 60/474,652, filed on May 30, 2003.

(51) Int. Cl.
| | |
|---|---|
| *A01N 43/04* | (2006.01) |
| *A61K 31/70* | (2006.01) |
| *A61K 31/715* | (2006.01) |
| *A01N 31/00* | (2006.01) |
| *A61K 31/45* | (2006.01) |
| *A01N 55/02* | (2006.01) |
| *A61K 31/29* | (2006.01) |
| *A01N 59/16* | (2006.01) |
| *A61K 33/26* | (2006.01) |
| *C07C 59/10* | (2006.01) |
| *C07C 59/285* | (2006.01) |

(52) U.S. Cl.
USPC .............. 514/25; 514/53; 514/738; 514/502; 424/646; 562/587

(58) Field of Classification Search
USPC ........ 514/25, 53, 738, 502; 424/646; 562/587
See application file for complete search history.

(56) References Cited

U.S. PATENT DOCUMENTS

| | | | |
|---|---|---|---|
| 2,885,393 A | 5/1959 | Herb | |
| 3,275,514 A | 9/1966 | Saltman et al. | |
| 3,367,834 A | 2/1968 | Dexter et al. | |
| 3,536,696 A | 10/1970 | Alsop et al. | |
| 3,592,889 A | 7/1971 | Lindvall et al. | |
| 3,686,397 A | 8/1972 | Muller | |
| 3,794,722 A | 2/1974 | Taya | |
| 3,821,192 A | 6/1974 | Montgomery et al. | |
| 3,873,588 A | 3/1975 | Osawa et al. | |
| 3,886,267 A | 5/1975 | Dahlberg et al. | |
| 4,058,621 A | 11/1977 | Hill | |
| 4,104,078 A | 8/1978 | Barker et al. | |
| 4,180,567 A | 12/1979 | Herb | |
| 4,226,983 A | 10/1980 | Lane | |
| 4,370,476 A | 1/1983 | Usher et al. | |
| 4,749,695 A | 6/1988 | Schwengers | |
| 4,786,518 A | 11/1988 | Nakel et al. | |
| 4,927,756 A | 5/1990 | Schwengers | |
| 4,975,290 A | 12/1990 | Artz et al. | |
| 5,284,832 A | 2/1994 | Ferrari et al. | |
| 5,624,668 A | 4/1997 | Lawrence et al. | |
| 5,746,999 A | 5/1998 | Gries et al. | |
| 6,333,306 B1 | 12/2001 | Lehmann | |
| 6,372,715 B1 | 4/2002 | Kaltwasser et al. | |
| 6,440,545 B1 | 8/2002 | Hisano et al. | |
| 6,537,820 B2 | 3/2003 | Beck et al. | |
| 6,693,211 B2 | 2/2004 | Kumari et al. | |
| 6,977,249 B1 | 12/2005 | Andreasen et al. | |
| 2002/0049161 A1 | 4/2002 | Lehmann | |
| 2002/0076821 A1 | 6/2002 | Beck et al. | |
| 2003/0078266 A1 | 4/2003 | Kararli et al. | |

FOREIGN PATENT DOCUMENTS

| | | |
|---|---|---|
| DE | 3844065 A1 | 7/1990 |
| EP | 0563753 A1 | 10/1993 |
| GB | 879441 A | 10/1961 |
| JP | 2002-530345 T | 9/2002 |
| WO | 00/30657 | 6/2000 |
| WO | 03/098564 A1 | 11/2003 |

OTHER PUBLICATIONS

Burger et al. "A Novel Polynuclear Iron (III) Mixed Ligand Complex for Use in Parenteral Iron Therapy," Inorganica Chimica Acta, vol. 80, pp. 231-235, 1983.

(Continued)

*Primary Examiner* — Scarlett Goon
(74) *Attorney, Agent, or Firm* — Lerner, David, Littenberg, Krumholz & Mentlik, LLP

(57) ABSTRACT

A process for preparing parenteral iron-saccharidic complexes, and the complexes produced, comprising: (1) providing an aqueous solution or dispersion including (i) Fe(III) and (OH)$^-$ ions and (ii) at least one saccharide, to form a reaction mixture, where the molar ratio of (i):(ii) is about 30:1 to about 1:30; and the mixture temperature and pH are at or above the complex assembly point (CAP); and (2) maintaining temperature and pH at or above the CAP for a time sufficient to form an iron-saccharidic complex having a molecular weight of about 25,000 Daltons or more. Control of the temperature and pH efficiently produces a high molecular weight complex. The complex can be separated by precipitation, dialysis and/or column fractionation and, if desired, dried, e.g., lyophilized or spray dried. The process can controllably synthesize complexes of varying molecular weight and/or chemical composition, particularly sodium ferric gluconate and ferric hydroxide-sucrose.

22 Claims, No Drawings

(56) References Cited

OTHER PUBLICATIONS

Zapsalis, C. and R.A. Beck, 1985, "Food Chemistry and Nutritional Biochemistry," Chapter 6, John Wiley & Sons, pp. 315-321.
"Raising the Bar for Quality Drugs," Chemical and Engineering News, American Chemical Society, Mar. 19, 2001, pp. 26-31.
"Principles of Food Science," edited by O.R. Fennema, "Part II, Physical Principals of Food Preservation," M. Karel et al., pp. 237-263, Marcel Dekker, Inc. 1975.
Encyclopedia of Food Science, edited by M.S. Peterson et al.,"Water Activity in Relation to Food," D.H. Chou, pp. 852-857, AVI Publ. Co., Inc., 1978.
Smales, C.M., D.S. Pepper and D.C. James, 2000, "Mechanisms of protein modification during model antiviral heat-treatment bioprocessing of beta-lactoglobulin variant A in the presence of sucrose," Biotechnol. Appl. Biochem., Oct., 32 (Pt. 2) 109-119.
Zapsalis, C. and R.A. Beck, 1985, "Food Chemistry and Nutritional Biochemistry," Chapter 10, John Wiley & Sons, pp. 588-591.
Dreywood, R., "Qualitative Test for Carbohydrate Material," Indus. And Eng. Chem. Anal. Ed., 18:499 (1946).
Hodge, J.E. and B.T. Hofreiter, "Determination of Reducing Sugars and Carbohydrates," Methods and Carbohydrate Chem., p. 380-394.
Zapsalis, C. and R.A. Beck, "Food Chemistry and Nutrional Biochemistry," Chapter 6, John Wiley & Sons, pp. 353-354 (1985.
Wyatt, P., "Light scattering and absolute characterization of macromolecules," Analytica Chimica Acta. (1993) 272:1-40.
Zapsalis, C. and R.A. Beck, Food Chemistry and Nutritional Biochemistry, 1985, Chapter 1, pp. 23-26.
"Freeze Drying," van Nostrand's Scientific Encyclopedia, Eighth Ed., pp. 1382-1342, 1995.
Rao et al., "Fe(III) Complexes of D-Glucose and D-Fructose," Biometals, vol. 7, pp. 25-29, (1994).
Geetha et al., "Transition-Metal Saccharide Chemistry: Synthesis, Spectroscopy, Electrochemistry and Magnetic Susceptibility Studies of Iron(III) Complexes of Mono- and Disaccharides," Carbohydrate Research., vol. 271, pp. 163-175, 1995.
Rao et al., "Solution of Stability of Iron-Saccharide Complexes," Bioorganic and Medicinal Chemistry Letters, vol. 2, No. 9, pp. 997-1002, 1992.
Rao et al., "Transition Metal Saccharide Chemistry and Biology: Syntheses, Characterization Solution Stability and Putative Bio-relevant Studies of Iron-Saccharide Complexes," Inorganica Chemica Acta., vol. 297, pp. 373-382, Jan. 2000.
Studies on Iron Complexes I, Yakugaku Zasshi 78, 951-957 (1958); Tanabe and Okada, Full English text and CA abstract.
Studies on Iron Complexes II, Takeda Kenkyusho Nempo 21, 1-10 (1962), Full English text and CA abstract.
Tanabe and Okada, Studies on Iron Complexes IV, Takeda Kenkyusho Nempo 21, 20-25 (1962), Full English text and CA abstract.
Faich and Strobos, American Journal of Kidney Disease Online, Mar. 1999, vol. 33, No. 3, 9 pages.

"Rates of Reactions" from Rader's Chem4kids.com [online], [retrieved Nov. 19, 2009]. Retrieved from the internet http://www.chem4kids.com/files/react_rates.html.. Published on Oct. 21, 2001.
Nagy, L., Szorcsik, A. (2002) Equilibrium and structural studies on metal complexes of carbohydrates and their derivatives. Journal of Inorganic Biochemistry, vol. 89, p. 1-12.
Nissim et al., The Lancet., Apr. 1949, pp. 686-689.
Nagy et al., Inorganica Chimica Acta., 124; 55-59 (1986).
Office Action from Japanese Application No. 2006-515004, dated Oct. 13, 2010.
Mannich & Rojahm: "Colloidal nature of saccharated iron" Berichte Der Deutschen Pharmazeutischen Gesellschaft , Deutsche Pharmazeutische Gese Llschaft, Berlin, DE, vol. 32, Jan. 1, 1922, pp. 158-166 , XP009080235.
Geisser P et al: "Structure/Histotoxicity Relationship of Parenteral Iron, Preparations", Arzneimittel Forschung. Drug Rese Arch, ECV Editio Cantor Verlag, Aulendorf, DE, vol. 42 , No. 12, Jan. 1, 1992, pp. 1439-1452, XP001121211.
Danielson B G et al ; "Pharmacokinetics of Iron(III)-hydroxide sucrose complex after a single intravenous dose in healthy volunteers", Arzneimittel Forschung. Drug Research , ECV Editio Cantor Verlag, Aulendorf, DE, vol. 46 , Jan. 1, 1996, pp. 615-621, XP002319686.
Nissenson A R et al: "Sodium ferric gluconate complex in sucroseis safe and effective in hemodialysis patients: North American Clinical Trial" American Journal of Kidney Diseases the Off Icial Journal of the National Kidney Foundation Mar. 1999 LNKD—Pubmed:10070911, vol. 33, No. 3, Mar. 1999, pp. 471-482, XP002605218.
Tonkovic & Nagy-Czako: "Preparation and properties of Fe(iii)-sugar complexes" Inorganica Chimica Acta, Elsevier BV , NL LNKD—DOI:10.1016/S0020-1693(00)91291-X, vol. 80, Jan. 1, 1983 ,pp. 251-254, XP002424616.
Faich G et al: "Sodium Ferric Gluconate Complex in Sucrose: Safer Intravenous Iron Therapy Than Iron Dextrans" American Journal of Kidney Diseases, W.B. Saunders, Philadelpphia, PA, US, vol . 33 , No. 3, Mar. 1, 1999, pp. 464-470, XP009014641.
Warady B A et al: "Sodium ferric gluconate complex therapy in anemic children on hemodialysis" Pediatric Nephrology 200509 DE LNKDDOI:10. 1007/S00467-005-1904-Y, vol. 20, No. 9, Sep. 2005 , pp. 1320-1327, XP002605219.
Yee J et al: "Iron sucrose: The oldest iron therapy becomes new" American Journal of Kidney Diseases 20021201 US LNKDDOI: I0.1053/AJKD.2002.36853, vol. 40, No. 6, Dec. 1, 2002, pp. 1111-1121, XP002605220.
Muller, A. "Classification and Properties of Iron Preparations" Arzneimittel Forschung. Drug Research, ECV Editio Cantor Verlag, Aulendorf, DE, vol. 24, No. 6, Jun. 1, 1974, pp. 880-883, XP009049190.
Supplementary European Search Report, EP 04776157, dated Nov. 4, 2010.
Hodge, J.E. and E.M. Osman, 1976, Chapter 3, in "Food Chemistry," O.R. Fennema Ed., Marcel Dekkar, New York, pp. 92-96.
Chem Abstract for JP 33005647, Takeda, Jul. 28, 1958; Accession No. 53:19317e-f CA.
Tanabe and Okada, Tanabe and Okada, Studies on Iron Complexes III, Takeda Kenkyusho Nempo 21, Nov. 19, 1962.

SYNTHESIS OF HIGH MOLECULAR WEIGHT IRON-SACCHARIDIC COMPLEXES

CROSS-REFERENCE TO RELATED APPLICATIONS

This application claims the benefit of the filing date of U.S. Provisional Patent Application No. 60/474,652 filed May 30, 2003. This application is a continuation of U.S. application Ser. No. 10/853,951, filed on May 26, 2004, the disclosure of which is incorporated herein by reference.

BACKGROUND OF THE INVENTION

The present invention is directed to the synthesis of iron-saccharidic complexes comprising an active hematinic species suitable for medicinal use, e.g., for parenteral administration of a composition comprising such a complex to a human or an animal in need thereof. Iron deficiency can develop from many conditions or disorders, including those linked to renal disease, repeated kidney dialysis, and cancer treatment wherein low hematocrit levels may require erythropoietin treatment in combination with iron supplements. Other routes that compromise heme synthesis are known as well. Currently available iron supplements in a form suitable for parenteral administration to treat iron deficiency, include, for example, dextran and non-dextran containing compositions.

The non-dextran iron-containing complexes or compounds (iron-saccharidic complexes) disclosed in patent and journal literature typically have a relatively low molecular weight, e.g., up to about 2500 Daltons or less. Many of these low molecular weight compounds are suited only for oral administration, not parenteral therapeutic use (See, e.g., Montgomery et al., U.S. Pat. No. 3,821,192; Rao et al. "Fe(III) Complexes of D-Glucose and D-Fructose," Biometals, vol. 7, pp. 25-29, 1994; Geetha et al. "Transition-metal Saccharide Chemistry: Synthesis, Spectroscopy, Electrochemistry and Magnetic Susceptibility Studies of Iron(III) Complexes of Mono- and Disaccharides," Carbohydrate Research, vol. 271, pp. 163-175, 1995; Rao et al. "Solution Stability of Iron-Saccharide Complexes," Bioorganic and Medicinal Chemistry Letters, vol. 2, No. 9, pp. 997-1002, 1992; Rao et al. "Transition Metal Saccharide Chemistry and Biology: Syntheses, Characterization, Solution Stability and Putative Biorelevant Studies of Iron-Saccharide Complexes," Inorganica Chimica Acta, vol. 297, pp. 373-382, January 2000; Burger et al. "A Novel Polynuclear Iron (III) Mixed Ligand Complex for Use in Parenteral Iron Therapy," Inorganica Chimica Acta, Vol. 80, pp. 231-235, 1983). Hematinic products based on polymeric saccharides or polysaccharides such as starch, cellulose, dextran and dextrin are not useful in the present invention. In particular, dextran and dextrin polysaccharides can have molecular weights of about 40,000 to about 75,000 or more.

A non-dextran iron-saccharidic complex is commercially available, for example, under the tradename "Ferrlecit" (Watson Pharmaceuticals, Inc.); the product is identified as sodium ferric gluconate complex in sucrose (SFGCS). The manufacturer states that the structural formula of the product is considered to be $[NaFe_2O_3(C_6H_{11}O_7)(C_{12}H_{22}O_{11})_5]_n$, where n is about 200, and as having an apparent molecular weight of 289,000-440,000 Daltons; based on the above structural formula, the formula weight is 417,600. The commercial hematinic composition is further described as the sodium salt of a ferric ion carbohydrate complex in an alkaline aqueous solution with approximately 20% sucrose, wt./vol. (195 mg/mL) in water, pH 7.7-9.7.

Another commercially available, non-dextran hematinic, marketed under the tradename "Venofer" (American Regent Laboratories, Inc.), is compositionally described as ferric hydroxide-sucrose complex (FHSC). The descriptive name suggests a form of ferric iron, i.e. Fe(III), that is present in a complex with sucrose.

Interestingly, synthetic routes for preparing commercially available parenteral hematinics, including those useful for treating humans, are believed to be unknown in the literature and the molecular structures of the resulting hematinics are poorly characterized. Only recently has a method for obtaining accurate reference standards been published (See U.S. Pat. No. 6,537,820, R. A. Beck and R. A. Mateer, Jr.; assigned to Chromaceutical Advanced Technologies, Inc.).

Iron-saccharidic complexes with hematinic activity generally contain iron atoms as Fe(III) (i.e., iron in the ferric valence state) which is believed to be necessary for hematopoiesis. Additionally, such complexes will include Fe(III) as part of a high molecular weight structure which is necessary in order to be useful for parenteral administration in humans. Iron-saccharidic complexes should be capable of delivering therapeutically useful iron for hematopoiesis over an extended period of time, e.g., for at least one day after administration and preferably over a period of several days after administration. However, localized administration of highly concentrated iron in the form of low molecular weight iron-saccharidic compounds or complexes are not subject to slow release and may produce adverse side effects, including toxicity. Such effects may be exhibited as localized damage at an injection site or unpredictable systemic responses in humans or animals in the form of shock, anaphylaxis, vascular hypotension, lethality or other indications of intolerance to the drug.

There is a continuing need in the field of therapeutic parenteral iron supplements for a well-defined synthesis method to which modern control and analytical methods can be applied and compositions produced thereby. Such an improved process can facilitate the manufacture of a product having enhanced purity. The present invention relates to the preparation or synthesis of therapeutically active iron-containing compounds and compositions, particularly useful in compositions comprising parenteral hematinic pharmaceuticals. Unique iron complexes are also described.

SUMMARY OF THE INVENTION

A process for the preparation of an iron-saccharidic complex, the complex suitable for potential administration in a mammal, comprising: (1) providing an aqueous solution or aqueous dispersion including (i) Fe(III) ion in the presence of (OH)$^-$ ion and (ii) at least one saccharide in order to form a reaction mixture wherein the molar ratio of (i):(ii) is about 30:1 to about 1:30 in said reaction mixture; the temperature and pH of said reaction mixture are at or above a complex assembly point; and (2) maintaining the temperature and pH at or preferably above the complex assembly point for a period of time sufficient to form an iron-saccharidic complex having a molecular weight of about 25,000 Daltons or more. Preferably, while the temperature in step (1) is at or above the complex assembly point, it is below a level that would cause undesirable precipitation of an Fe(III) compound or composition, and most preferably below about 75° C. Optionally, the temperature in step (2) can be increased relative to the temperature in step (1) to at least about 80° C., which is an efficient way to produce high molecular weight iron-saccharidic complexes. The high molecular weight complex can be separated from the reaction mixture by various methods, including precipitation, dialysis and/or column fractionation.

The process suitably synthesizes a broad range of iron-saccharidic complexes of varying molecular weight and/or chemical composition in a controlled manner, particularly sodium ferric gluconate complexes and ferric hydroxide-sucrose complexes. If a solid product is desired, the iron-saccharidic complex can be dried in various ways, e.g., lyophilized or spray dried. Non-dextran, iron-saccharidic complexes of the present invention can include SFGCS, FHSC and mixtures thereof, as well as other iron-saccharidic complexes, which have been or can be synthesized using the technology disclosed herein. Furthermore, the iron-saccharidic complexes of the present invention can be used to prepare parenteral iron pharmaceutical compositions useful for treating human or animal subjects in need of supplemental iron therapy.

DETAILED DESCRIPTION

The present invention provides a simple, yet elegant, synthesis scheme suitable for producing a variety of iron-saccharidic complexes. Consequently, such products can be produced with fewer undesirable by-products that can translate into improved pharmaceutical qualities.

For purposes of the present invention a "hematinic" means a compound or composition including iron in a form that tends to increase the number of erythrocytes and/or the hemoglobin concentration in the blood of a mammal, particularly in a human. Consequently, an iron-saccharidic complex of the present invention is, or contains, an active hematinic species or AHS. These complexes also contain iron in the form of Fe(III) and saccharide, usually in the form of anions. For purposes of the present invention, such iron-saccharidic complexes exclude the iron-dextrans of the art. Examples of iron-saccharidic complexes that can be produced using the present invention include such species as sodium ferric gluconate complex in sucrose (SFGCS) and ferric hydroxide-sucrose complex (FHSC).

For purposes of the present invention, reference to Fe(III) and $(OH)^-$ as "ions" includes these entities individually as well as their presence in larger ionic species, e.g., $Fe(OH)_2^+$ or $FeOH^{2+}$ or $Fe(OH)_4^-$ etc.

The term "complex" can have alternative meanings in various contexts in this art. In one meaning, the term complex may be used to describe the association between two or more ions to form a relatively low molecular weight, non-polymeric composition that exists or operates as a single entity under a given set of conditions. This type of "complex" has been referred to as a "primary complex." Alternatively, the term complex has been used to describe an association or aggregation of a plurality of primary complexes having the characteristics of a larger macromolecule. Such a complex is sometimes referred to as a "secondary complex." For purposes of the present invention, the term "complex" refers to these larger aggregations. In view of their molecular weight, such complexes are also sometimes characterized as being high molecular weight macromolecules.

Furthermore, it will be appreciated that the term "complex" as used herein particularly refers to high molecular weight macromolecules or aggregations of Fe(III) and certain saccharides, whether primary complexes are formed or not. Thus, in its broadest sense, the term "complex" as used herein refers to molecules, aggregates or associations of Fe(III) and certain sugars, in the form of reaction products, which attain an absolute weight average molecular weight of about 25,000 Daltons and preferably higher, e.g., 100,000 and higher. For purposes of the present invention, the following terms have the indicated meanings, adapted from Hawley's Condensed Chemical Dictionary, $13^{th}$ Ed., Revised by R. J. Lewis, Sr., (John Wiley & Sons, 1997): a "suspension" is a system in which very small particles, in the present invention such particles are of colloidal size, e.g., about 1 to about 100 nm, are more or less uniformly dispersed in a liquid medium, and also in the present invention, typically an aqueous medium such as water. A colloidal suspension is also referred to as a colloidal solution and often referred to in the literature as a "solution." In the present invention, the term solution is used interchangeably with colloidal solution, colloidal suspension, or colloidal dispersion. In each instance, it is understood that the colloidal sized particles are the complexes synthesized by the methods of the present invention. Furthermore, a "dispersion" is a two-phase system where one phase comprises finely divided particles, and, as noted, in the present invention such particles are of colloidal size, distributed throughout a bulk substance, e.g., a water phase, the particles being the disperse or internal phase, and the bulk substance the continuous or external phase. As noted above, solid-in-liquid colloidal dispersions are also sometimes referred to as solutions.

For purposes of the present invention, the general term "excipients" includes components, compounds and complexes that do not exhibit the desired hematinic response, e.g., to counteract iron deficiency, including synthesis reaction by-products and unreacted starting materials, degradation by-products, diluents, buffers, preservatives, salts, etc., that are present in admixture with therapeutically active iron-containing species such as iron-saccharidic complexes. Particularly undesirable excipients are generally those that result from the process for synthesizing the AHS or from degradation of the AHS after synthesis, e.g., typically as a result of post-synthesis processing or as a consequence of storage. Excipients intentionally added to a parenteral composition comprising the AHS are to be distinguished from such undesirable excipients. Intentionally added excipients are more accurately characterized and identified as "additives" in order to distinguish them from the above-described undesirable excipients or merely, "excipients."

Parenteral administration of a substance, e.g., a drug or, in the present case, an iron-saccharidic complex of the present invention, refers to introduction by some means other than through the gastrointestinal tract. In particular, it includes intradermal, intravenous, subcutaneous, intramuscular, intra-articular, intrasynovial, intraspinal, intrathecal, intracardiac or intramedullary injection or prolonged infusion of about 30 minutes or longer.

The iron present in the iron-saccharidic complexes of the present invention is in the form of Fe(III) or ferric, not ferrous, Fe(II). Useful saccharides include, inter alia, sugars and sugar derivatives. "Sugars" include, for example, the monosaccharide aldose such as glucose. "Sugar derivatives" include derivatives of sugars such as carboxylated glucose known as gluconic acid. Gluconic acid is a glucose oxidation product. Glucitol, also known as sorbitol, is a glucose reduction product and is also a sugar derivative. Both the original monosaccharide, e.g., glucose, and its reaction products retain evidence of the characteristic saccharide group although now in an oxidized or reduced form. The oxidized saccharide group includes a carboxyl group which, under appropriate pH conditions, can ionize according to its ionization constant and $pK_a$ value. When ionized, the oxidized saccharide group can be denoted as a "saccharate" or it can be described as a saccharidic acid where the ionizable proton remains with the oxidized saccharide group. If the ionized carboxyl group of the saccharide group is associated with a cation such as sodium, a saccharidic acid salt is formed. For example, oxidation of glucose gives gluconic acid and the sodium salt of this saccharidic acid is sodium gluconate. Other suitable sugar derivatives include those that react in a similar manner as sugar or the sugar derivatives recited immediately above in the process of the present invention. A useful derivative is isoascorbic acid, also known as erythorbic acid or D-araboascorbic acid. Upon reaction in the process of the present invention isoascorbic acid forms the intermediate 2,3-diketogluconic acid. The latter is also believed to be an intermediate that is formed in reactions in which sugars are used as a starting material.

Monosaccharides that are aldoses commonly undergo oxidation to give their saccharidic acid equivalents or, when ionized, monosaccharate forms may interact with selected cations having valence states of +1 to +3.

Glyceraldehyde is the simplest structure that demonstrates such an ald-group, another form of sugar derivative, while dihydroxyacetone serves as a corresponding example of a sugar derivative including a keto-group. Extensions of such structures with six carbon atoms account for two carbohydrate classifications, one form being aldoses and the other ketoses.

The present invention provides a process for preparing or synthesizing a high molecular weight, non-dextran containing iron-saccharidic complex suitable for parenteral administration to mammals, including both people and animals.

Reactants useful in the process of the present invention include the following components. The order listed below does not imply an order of addition in the process; such process details are described hereinafter.

At least one saccharide. As previously described, this can include a sugar or sugar derivative. For purposes of the present invention the term "sugar" includes monosaccharides, oligosaccharides (a saccharide containing up to about ten simple sugars linked together and, therefore, a disaccharide is included within the definition of oligosaccharide). "Sugar derivatives" include compounds derived from such monosaccharides and oligosaccharides, e.g., by reduction of a carbonyl group (alditols), by oxidation of one or more terminal groups to carboxylic acids, by replacement of one or more hydroxy group(s) by a hydrogen atom, an amino group, a thiol group or similar heteroatomic groups, etc. It also includes further derivatives of these compounds. In some instances simplified references have been used herein as a shorthand to formal classes of derivatives found in the literature, e.g., the term "alcohol derivatives" has been used herein as equivalent to the more formal term "alditols." For purposes of the present invention:

The generic term "monosaccharide" (as opposed to oligosaccharide or polysaccharide) denotes a single unit, without glycosidic connection to other such units. It includes aldoses, dialdoses, aldoketoses, ketoses and diketoses, as well as deoxy sugars and amino sugars, and their derivatives. Consequently, the term monosaccharide includes both sugar and sugar derivatives referred to in the present invention.

Aldoses and ketoses: monosaccharides with an aldehydic carbonyl group are called aldoses; those with a ketonic carbonyl group, ketoses. Ketoaldoses (aldoketoses, aldosuloses) are monosaccharides containing a aldehydic group and a ketonic group.

Deoxy sugars: monosaccharides in which an alcoholic hydroxy group has been replaced by a hydrogen atom are called deoxy sugars.

Amino sugars: monosaccharides in which an alcoholic hydroxy group has been replaced by an amino group are called amino sugars; when the hemiacetal hydroxy group is replaced, the compounds are called glycosylamines.

Alditols: the polyhydric alcohols arising formally from the replacement of a carbonyl group in a monosaccharide with a CHOH group are termed alditols, including, e.g., glycerol.

Aldonic acids: monocarboxylic acids formally derived from aldoses by replacement of the aldehydic group by a carboxy group are termed aldonic acids.

Ketoaldonic acids: oxo carboxylic acids formally derived from aldonic acids by replacement of a secondary CHOH group by a carbonyl group are called ketoaldonic acids.

Uronic acids: monocarboxylic acids formally derived from aldoses by replacement of the $CH_2OH$ group with a carboxy group are termed uronic acids.

Aldaric acids: The dicarboxylic acids formed from aldoses by replacement of both terminal groups (CHO and $CH_2OH$) by carboxy groups are called aldaric acids.

Glycosides: glycosides are mixed acetals formally arising by elimination of water between the hemiacetal or hemiketal hydroxy group of a sugar and a hydroxy group of a second compound. The bond between the two components is called a glycosidic bond.

Oligosaccharides: Oligosaccharides are compounds in which monosaccharide units are joined by glycosidic linkages. According to the number of units, they are called disaccharides, trisaccharides, tetrasaccharides, pentasaccharides etc. Oligosaccharides useful in the present invention include those having about 2 to about 10 units. In contradistinction to polysaccharides, the term "oligosaccharide" is commonly used to refer to a defined structure as opposed to a polymer of unspecified length or a homologous mixture. When the linkages are of other types, the compounds are regarded as oligosaccharide analogues, which can also be useful. Disaccharides in particular are within the scope of the present invention.

Sugars useful in the present invention include both monosaccharides and disaccharides including those that are referred to as simple sugars as well as complex sugars. Typical monosaccharides are $C_3$-$C_6$ compounds and include dihydroxyacetone, glyceraldehyde, erythrose, ribose, ribulose, sorbose, xylose, and arabinose, as well as the more common sugars such as fructose (also known as levulose) and glucose (also known as dextrose), and also galactose, and mannose. Disaccharides include, without limitation, sucrose, maltose, cellobiose, gentiobiose, isomaltose, melibiose, primeverose, rutinose, trehalose and lactose.

Particularly useful sugars, as well as sugar derivatives, are, to a greater or lesser extent, substantially water soluble at, e.g., ambient temperature (e.g., about 20° C. to about 25° C.), or at temperatures somewhat elevated above ambient temperature (e.g., about 25° C. to about 50° C., further depending on the concentration of the particular saccharide(s) as well as other reactants present. Both naturally occurring and synthetic sugars and sugar derivatives are useful, including, when they exist, the optically active rotatory forms, i.e., those forms that demonstrate right or left optical rotation of polarized light; in other words, including both the D (or plus, +) and L (or minus, −) enantiomeric forms as well as the racemic mixture.

Useful sugars include those characterized as reducing sugars as well as the non-reducing types. Glucose and maltose are typical examples of reducing sugars, containing an aldehyde group that is considered the basis for the characterizing reducing reaction. Sucrose is an example of a non-reducing sugar.

In contrast to the classes of saccharides useful in the present invention, polymeric saccharides or polysaccharides such as starch, cellulose, dextran and dextrin are not useful. Thus, the iron-saccharidic complexes of the present invention are preferably free of anything other than inconsequential amounts of polysaccharides, e.g., substantially polysaccharide free. In particular, the iron-saccharidic complexes do not contain concentrations of polysaccharides that would cause adverse, particularly severe allergic, reactions in patients to whom such an iron-saccharidic complex is parenterally administered.

Sugar derivatives are saccharides useful in the present invention, including acids, salts, methyl esters, acetates, amines, and alcohols based on any of the forgoing sugars. Acids include: gluconic acid; glucaric acid; the hydroxy acid of fructose; $\alpha$-methylcaproic acid; aldonic acids; aldaric acids; mannaric acid; uronic acids; galacturonic acid; glucuronic acids; mannuronic acids; xylaric acid; tartaric acid; mucic acid; glyceric acid; lactic acid; tartaric acid; dicarboxylic acids of arabinose, glucose and mannose; maltobionic acid; and lactobionic acid. Salt derivatives of sugars include the alkali metals and alkaline-earth metals of sugar acids, including metals selected from the group consisting of lithium, sodium, potassium, calcium, barium, strontium and magnesium. A particularly useful salt is sodium gluconate. Amines include, for example, fucosamine (also known as 2-amino-2,6-dideoxygalactose), galactosamine (or 2-amino-2-deoxyglactose), acosamine (or 3-amino-2,3,6-trideoxy-L-xylo-hexose), bacillosamine (or 2,4-diamino-2,4,6-trideoxy-D-glucose), glucosamine (or $CH_2OH(CH_2O)_3CHNH_2$ CHO), etc. Alcohols include, for example, mannitol, sorbitol (more accurately, glucitol), arabinitol, xylitol, fucitol, rhamnitol, erythritol, ribitol, galactitol, glycerol, etc.

The process further utilizes (2) a soluble or dispersed ferric, i.e., Fe(III), compound, including such iron in the form of Fe(III) ion. Specific compounds useful as sources of Fe(III) include ferric chloride, ferric nitrate, ferric hydroxide, ferric sulfate, ferric acetate, ferric carbonate, and ferric citrate; ferric hydroxide is especially useful. The formula of ferric hydroxide can be represented as $Fe(OH)_3$ or $Fe_2O_3.3H_2O$. Ferric salts, such as those just named as well as any others that can be useful in this process, are typically used in the present invention as a means of generating ferric hydroxide in situ. Preferably, the ferric salt is at least partially soluble in water and capable of being converted to the hydroxide under the conditions of the process.

Especially useful is ferric hydroxide in a colloidally dispersed form. A colloid is typically considered to be a physical state intermediate between a true solution and a suspension. For purposes of the present invention, a "true solution" means a uniformly dispersed mixture at the molecular or ionic level, of one or more substances, the solute or solute phase, in one or more other substances, the solvent or solvent phase. Useful colloid particle sizes, particularly for ferric hydroxide, include particle sizes of about 1 to about 100 nanometers. An aqueous colloid is sometimes referred to as a hydrosol, so that a ferric hydroxide hydrosol is a ferric hydroxide colloid in water. For purposes of the present invention the term "solution" will be understood to include a "true" solution as well as a dispersion, colloid, hydrosol and mixtures of such states, e.g., an aqueous mixture including a sugar solution and a ferric hydroxide hydrosol.

The reaction used to produce an iron-saccharidic complex of the present invention is preferably carried out in an aqueous or substantially aqueous reaction medium. By "substantially aqueous" it is meant that the fluid reaction medium can include non-aqueous components of a type and in a concentration that does not prevent synthesis of the iron-saccharidic complex. However, at least some water must be present; preferably at least a majority of the diluent present is water. The reactions contemplated by the process can be carried out in a reactor of any suitable size for the volume of reactants necessary to produce the amount of product desired. Furthermore, the reactors and related equipment can be constructed of any sufficiently corrosion-resistant material suitable for the reactions to be conducted, including, e.g., various metals such as copper, stainless steel or other metal alloys. In particular, the reactor can be constructed of a metal or metal alloy resistant to corrosion by the reactants at the pH levels used, further including reactors lined with glass or synthetic plastic. Alternatively, glass reactors can be used. Preferably the reactors are glass or glass lined so as to produce products that are free of trace metal contaminants.

The reactants can be introduced as aqueous solutions, suspensions, dispersions or colloidal suspensions. At least some of the reactants, e.g., at least one saccharide such as sugar or a sugar derivative, can be introduced as a particulate solid and dissolved or dispersed in water or a diluent prior to carrying out the reaction. The source of ferric ion, if not provided as a ferric hydroxide solution, is typically introduced as a salt, e.g., ferric chloride, in aqueous solution. Preferably the salt is reacted with a base, e.g., sodium carbonate, to convert it to ferric hydroxide, i.e., there will then be present in the reaction mixture ferric ion in the presence of $(OH)^-$ ion. Ferric hydroxide formed in situ can be in solution, but it is typically in a dispersed or colloidal form; a colloid being most preferred. Generally, colloids can be prepared by mechanical crushing, irradiation with ultrasonic waves, electrical dispersion as well as chemical methods; chemical methods are particularly useful in the present invention. Preparation methods for forming ferric hydroxide colloids, particularly useful in magnetic recording media, are described in U.S. Pat. No. 6,440,545, incorporated herein by reference to the extent permitted.

These methods include adding an aqueous solution of alkali hydroxide or alkali carbonate to an aqueous solution of a ferric salt, e.g., ferric chloride or ferric sulfate, and then oxidizing the reactants by bubbling an oxygen-containing gas into the mixture. Another method involves adding an aqueous solution of an alkali hydroxide to an aqueous solution of a ferric salt at a concentration with respect to the ferric ion sufficient to form a precipitate at a temperature of 5° C. or higher and raising the temperature to a higher value.

The preparation of an aqueous colloidal dispersion supersaturated with ferric hydroxide is also described as a preliminary step in the preparation of storage stable organic sols in U.S. Pat. No. 6,271,269, incorporated herein by reference to the extent permitted. The patent describes reactant concentrations and pH conditions necessary to produce the desired colloid. For example, useful ferric salts include any aqueous solution of a ferric salt, in particular, ferric chloride and ferric nitrate. The basic medium or reactant is, e.g., an aqueous solution of ammonium, sodium or potassium hydroxide. Preferably the iron salt solution is selected such that it contains no more than 5% of anions that are coagulating. The concentrations of the aqueous iron salt solution and aqueous basic solution are described and adjusted according to equations set forth in column 5 of the patent. The reaction mixture is heat treated at from 15° C. to 80° C. for from 5 minutes to 8 hours. A colloidal dispersion is obtained in which the colloidal particle sizes range from 100 to 700 Å. While a supersaturated aqueous ferric hydroxide solution is not required in the present invention, this reference provides a potentially useful option.

For purposes of the present invention, the preparation of ferric hydroxide by hydrolysis of a ferric salt also can be accomplished using salts such as ferric chloride, ferric nitrate, ferric acetate, ferric sulfate, and double salts, including, e.g., ferric ammonium sulfate and ferric potassium sulfate, and mixtures thereof. The hydrolysis co-reactant can be an alkali metal hydroxide or carbonate, including, for example, sodium hydroxide, potassium hydroxide and sodium carbonate. While it is possible to start with a ferrous compound, e.g., a salt or hydroxide, and oxidize the ferrous ion to ferric ion, the pharmaceutically acceptable complex requires ferric ion, Fe(III). Consequently, if a ferrous compound is used, care needs to be taken to remove residual ferrous-containing unreacted reagent or by-products. Overall, the use of a starting material based on ferric ion is preferred.

Contacting of the saccharide, e.g., sugar and/or sugar derivative, with the ferric compound, e.g., ferric hydroxide, is preferably conducted under controlled conditions of temperature and pH.

Typically, an aqueous solution of a ferric salt is first prepared, but ferric hydroxide can be separately prepared or purchased for use in the process of the invention. Where a ferric salt is used, an aqueous solution of the salt will have an equilibrium or initial pH that will vary depending on the specific salt that is used. For example, the pH of a ferric chloride solution useful in the process of the present invention is typically about 1.7. A basic additive, e.g., sodium carbonate, $Na_2CO_3$, is introduced, typically as a solution; the mixture is preferably being well-stirred during this operation. Optionally, but preferably, during this step of the process the mixture is gently heated; e.g., typically to a temperature of about 20° C. to about 75° C.; preferably about 25° C. to about 70° C.; more preferably about 40° C. to about 65° C.; for example, about 25° C. to about 50° C. Excessive heat at this stage is undesirable. For example, a temperature of greater than about 75° C. creates the potential to oxidize and/or coagulate and precipitate the ferric hydroxide, neither of which is useful. Mixing and heating of the mixture can facilitate removal of $CO_2$ generated by the reaction when, e.g., $Na_2CO_3$ is employed. If a different basic material is used, such mixing and moderate heating can encourage completion of the reaction. Optionally, a vacuum can be applied to further assist in the removal of the carbon dioxide.

When sufficient base has been added at this stage in the process to convert substantially all of the ferric salt to ferric hydroxide, the pH of ferric hydroxide hydrosol is typically about 1.5 to about 2. Although additional base can be added, care should be taken to avoid excessive base that may result in precipitation of ferric hydroxide to an extent that will interfere with the formation of an iron-saccharidic complex. Preferably, the reactants are mixed or stirred during this and later stages of the process in order to facilitate contact and reaction between the components. Various conventional means can be employed to accomplish such mixing, including, for example, the use of a continuous stirred tank reactor, optionally including heating and/or cooling means such as a heating mantle, heat exchanger tubes, etc.

After ferric hydroxide has been formed, at least one saccharide (sugar and/or sugar derivative) is added. It is particularly preferred that the saccharide be added after the majority, substantially all, and more particularly all, of the ferric salt has been converted to the hydroxide, as indicated, e.g., by the absence of additional $CO_2$ generation where sodium carbonate is used as a reactant. The saccharide can be added as a solid or can be dissolved or dispersed in water prior to adding it to the ferric hydroxide component.

The pH of this mixture is preferably increased, typically by addition of a basic material. For convenience, this stage of the process can be referred to as the titration step. Preferably, but not necessarily, the same basic material is used as was used in the forming the ferric hydroxide. As an example, ferric chloride and sodium carbonate are contacted in an aqueous system to form ferric hydroxide hydrosol; preferably the aqueous mixture is well stirred during this step and thereafter. The pH of this hydrosol is typically about 1 to about 2, marking the complete, or substantially complete, conversion of the ferric chloride to ferric hydroxide. Provided that sufficient ferric hydroxide is present for formation of the iron-saccharidic complex, it is not necessary that all of the ferric salt originally added to the reactor be converted to ferric hydroxide. Furthermore, at the conclusion of the process it is preferred that unconverted ferric salt and/or unreacted ferric hydroxide, if any, be separated from the iron-saccharidic complex. Sodium gluconate is added to the mixture. Additional sodium carbonate, preferably in the form of a more concentrated solution than initially used to form the ferric hydroxide hydrosol, is added incrementally to the mixture while monitoring the pH and/or appearance and condition of the mixture until the desired end-point is reached.

As a consequence of this further addition of basic material, changes can be observed in the reaction mixture. In addition to an increase in pH, a color change can be observed in the reaction mass. An aqueous solution of a ferric salt such as ferric chloride typically has a yellow color. Addition of a base, for example, sodium hydroxide or sodium carbonate, produces ferric hydroxide and a color change to red or reddish-brown at a pH of greater than about 1 to about 3. While not wishing to be bound by theory, it is believed that a further increase in pH caused by the addition of still more basic material causes an increase in the size or aggregation of the colloidal particles of ferric hydroxide sufficient to be observed as a further color change. In particular, as the additional basic material is added, a milky brown color can be observed to form in the area of the mixture where the basic material is introduced; it can be appreciated that the localized concentration of base is high at that point in the mixture until the added base is dispersed as a result of mixing. This is not unlike a titration reaction approaching its end-point. As still more basic material is added and the pH increases further, the color change eventually persists throughout the reaction mixture. Provided that the temperature is sufficiently high, e.g., greater than about 20° C., it is believed that at about the point where the color change persists in the mixture, the ferric hydroxide can also react with the sodium gluconate. However, it is possible that by this point, the reaction that forms the iron-saccharidic complex has already begun, particularly in the immediate region in the mixture where the base is added. As still more basic material is added, the color of the mixture changes to a deeper red-brown, then the milky appearance dissipates and the mixture appears to clarify, retaining a deep red-brown color. Although the mixture appears to be clear at this point, it is believed that the ferric hydroxide and/or iron-saccharidic complex is present in colloidal form rather than as a true solution. In either event, it is believed that the iron-saccharidic complex is present.

Further evidence for the formation of an iron-saccharidic complex based on color and appearance of the reaction mixture has been observed based on comparative experiments in which titration was conducted by adding sodium carbonate to a ferric chloride solution in the absence or in the presence of sodium gluconate. When the addition of base, e.g., sodium carbonate, is conducted in the absence of sodium gluconate, the reaction mixture has a milky appearance at a pH of about 3 to about 6, and continued addition of sodium carbonate results in the formation of a gross precipitate; the mixture does not become clear. In contrast, when the addition of base is conducted in the presence of sodium gluconate, the mixture takes on a milky appearance at a pH of about 3 to about 3.5 and continues to have a milky appearance to a pH of about 6. However, still further addition of sodium carbonate causes the mixture to clarify and the color to change to a deep red-brown at a pH of about 9. Prior to complete clarification, addition of a droplet or small quantity of the aqueous solution of the base causes the mixture to become clear and deeply red-brown in color in the immediate vicinity of the droplet. As the added base is stirred or dispersed into the body of the reaction mixture the overall cloudy appearance returns until the "endpoint" for the reaction is reached, at which point the mixture clarifies and becomes deeply colored as described above. This suggests that most, if not all, of the ferric hydroxide originally present is converted to the iron-saccharidic complex at a higher pH, but at least some is believed to have formed at a lower pH, e.g., about 6. In any event, it should be understood that the transitional and end points described above with regard to pH can further depend on the concentration, relative reactant ratios and temperature at which the reaction is conducted.

Appearance of color in the reaction mixture and the color attained by the solution can be used as a process control tool. Again, provided that the mixture temperature is sufficient, the initial appearance of a milky brown color indicates a possible change in size and the occurrence of possible complexation. Without wishing to be bound by theory, it is believed that the point at which the milky brown color persists substantially throughout a reaction mixture comprising ferric ion in the presence of (OH$^-$) and saccharide, even with thorough mixing, indicates that the reaction conditions, including a combination of pH, temperature and concentration, are sufficient to achieve complexation and that such complexation is capable of continued, self-sustaining, reaction. For convenience, this condition is referred to as the "complex assembly point." However, it is possible that the complex assembly point could be reached independent of color change. Therefore, while color change can be a useful tool, it is not intended to be a limiting variable.

The complex assembly point depends on the interaction of several variables within the reaction mixture for formation of an iron-saccharidic complex. Consequently, it is convenient to refer to the complex assembly point rather than to individual values or a range of values for each of the process variables: ferric ion concentration; pH; saccharide type (or types if a mixture is used) and concentration; and temperature. For a given system of the present invention, the complex assembly point is the minimum set of conditions that is necessary to allow for the formation of iron-saccharidic complexes having an absolute weight average molecular weight of about 25,000 Daltons or more, e.g. about 100,000 Daltons or more. For example, if component concentrations and pH are sufficient, but the temperature is too low, the complex assembly point will not have been established and maintaining the reaction mixture at, e.g., a pH of about 5.5 at a temperature of about 20° C. even for an extended time period will not produce an iron-saccharidic complex or may produce it in a time-frame that is not practically or commercially feasible. Under the conditions of this example, increasing the temperature, e.g., to about 60° C., can be sufficient for the iron-saccharidic complex to form, particularly in useful quantities, overnight. Furthermore, it is to be understood that, while the complex assembly point may be achieved by a minimum set of conditions, increasing one or more of the control variables, particularly pH and temperature, can result in a more efficient reaction and, possibly, better control of molecular weight and/or molecular weight distribution of the iron-saccharidic complex.

A useful instrument for assessing color and color change is the Hunter Color Difference Meter (Hunter Associates Laboratory, Alexandria, Va.). This instrument measures reflected and transmitted light and produces results in terms of L, which is a lightness function (black-white axis); a, which predicts redness (red-green axis); and b, which predicts yellowness (yellow-blue axis). Calculation methods are well known to those skilled in the art, and typically are based on standards of the International Commission on Illumination, or CIE.

It is possible to add the saccharide to the ferric hydroxide hydrosol after the pH has been elevated from about 2 to, for example about 6, provided that the addition of base does not result in an undesirable amount of ferric hydroxide precipitation and thereby removal of Fe(III) from the reaction mixture prior to addition of the saccharide. Alternatively, the ferric hydroxide can be formed or added after achieving a pH level that is above that of the complex assembly point, eliminating the need for the subsequent addition of base. However, when a titration step is used and when the complex assembly point is reached or exceeded, it will be observed that the pH of the mixture has increased significantly from the starting pH of the original ferric hydroxide/sugar mixture, provided that excess base was not used beyond that required to convert substantially all of the ferric salt present in the reaction mixture to ferric hydroxide. For example, if the pH of the mixture is originally at a level of about 2 to about 3 when the ferric hydroxide hydrosol is formed, the pH at the complex assembly point may be about 5.0 or more; alternatively, about 5.3 or more; for example, about 5.5 or more; or about 5.7 or more; or about 6 or more. The pH level sufficient to reach or exceed the complex assembly point will depend on the process conditions, particularly the temperature and reactants, saccharide or saccharide mixture, present in the reaction mixture. It is particularly preferred that the addition of basic material is stopped prior to the point at which the reaction mixture becomes clarified, usually a pH of about 9 or less. However, where sucrose, and, possibly, other non-reducing sugars are used, to achieve the complex assembly point the basic material preferably is a stronger base such as sodium hydroxide and sufficient basic material is added to increase the pH to a more basic condition, e.g., to a pH of about 8.5 to about 9.5; for example, about 9.

It has surprisingly been observed that, for at least some processes in accordance with the present invention, if the addition of the basic material is stopped at or slightly beyond the complex assembly point but prior to the point at which the transition from a milky to a clear condition occurs in the reaction mixture (clarification typically occurring at a pH of about 7 to about 10, e.g., more typically about 9), and provided that the mixture is also at a sufficient temperature, further addition of base may be discontinued. In other words, having reached the complex assembly point, the reaction that forms the iron-saccharidic complex is thereafter capable of being self-sustaining, in terms of a further increase in pH, and potentially continuing substantially to completion, given sufficient time and maintenance of temperature. It may be observed that the pH of the reaction mixture that is at or beyond the complex assembly point can be higher at completion of the reaction than when the complex assembly point is reached; e.g., if the pH is originally about 6, it can be about 9 at completion without any intermediate pH adjustment.

The effect of reaction temperature also can be significant. At moderate temperature, for example, about 60° C., and a pH of about 6, it may require about 12 to about 18 hours, e.g., about 16 hours, for production of a high molecular weight iron-saccharidic complex. In contrast, with the addition of significant heat, for example, raising the temperature to about 95° C. to about 100° C. during the titration step or thereafter, at about the same pH, a high molecular weight iron-saccharidic complex can be produced in about 15 minutes.

Surprisingly, if the addition of the basic material is stopped substantially before the complex assembly point, then, even if the temperature is increased significantly thereafter, a pH test of the mixture may show a decrease in pH from the level at which the last addition of basic material has been made. This is believed to indicate that the conditions in the reaction mixture are insufficient for self-sustaining formation of a high molecular weight iron-saccharidic complex. A change in at least one of the controlling variables is necessary, e.g., increasing the pH by the addition of basic material, provided that the temperature is greater than at least about 20° C. With limited experimentation, the color condition of the reaction mixture described above can be used as a convenient indicator of reaction status. Therefore, based on the teachings herein, the process can be maintained within well-defined limits based on, e.g., the combination of temperature, pH in order to produce an iron-saccharidic complex having defined and controllable properties.

If basic material addition is continued to about the point where clarification occurs, continuation of the complexation reaction may result in a further increase in the pH of the mixture beyond a physiologically suitable level. For example, the pH of the high molecular weight iron-saccharidic complex may be greater than about 10; e.g., about 10.5 to about 11.5. Optionally, however, the reaction mixture can be taken to a higher pH level, even to the point of clarification or beyond, provided that the pH of the iron-saccharidic complex product is subsequently adjusted to a physiologically suitable level, for example, a pH of about 7.0 to about 9.0 using additives well-known in the art, including e.g., at least one buffer, by further dilution or changing the type of diluent.

Where ferric hydroxide is produced in situ from a ferric salt and a base, the temperature preferably is controlled at less than about 75° C., but is sufficiently high enough to reach or exceed the complex assembly point. Preferably the temperature is greater than about 20° C., for example about 25° C. to about 70° C.; more preferably about 40° C. to about 65° C.; alternatively, about 45° C. to about 70° C.; for example, about 45° C. to about 65° C. If the temperature is too low, e.g., about 20° C. or less, the complex assembly point is often not reached. A temperature of about 25° C. or higher is preferred; at temperatures between about 25° C. and about 50° C. while a complex may be formed, extended reaction time and/or reduced conversion may result. Conversely, too high a temperature at this stage of the process is unacceptable, e.g., greater than about 85° C.; for example, greater than about 75° C. If excessive heat is applied at this stage, the reaction mixture is susceptible to oxidation and coagulation resulting in no product or an unacceptable product. It has been observed that if the complex assembly point has been substantially attained, that even a moderate temperature is sufficient to produce the high molecular weight iron-saccharidic complex of the invention. For example, a significant yield of a sodium ferric gluconate complex having a molecular weight of about 3,300,000 has been produced by titrating at about 20° C. to a pH of about 6 followed by an increase in temperature to about 60° C. and a reaction time of about 16 hours.

Note that the absolute temperature is not important provided that it is at least at the complex assembly point and low enough to avoid substantial oxidation or precipitation of the reactants and/or product.

The reaction mixture is an aqueous based system, i.e., water is a component of the reaction mixture. Preferably the reactants are not contacted at excessively high concentrations since at least one of the effective reactants, ferric hydroxide, is preferably present in colloidal form and the iron-saccharidic complex also is preferably produced as a colloid. Excessively concentrated reactants can result in a reaction mixture that is unduly sensitive, e.g., susceptible to coagulation, due to slight variations in process conditions. Consequently, it is preferred that the reactants are contacted using the following concentrations as a guideline: aqueous sugar and/or sugar derivative solution, about 0.0046 M to about 0.46 M, preferably about 0.02 M to about 0.06 M; aqueous ferric salt solution about 0.01 M to about 3.00 M, preferably about 0.02 M to about 0.6 M; aqueous basic material such as sodium carbonate for attaining the reaction mixture pH, about 0.02 M to about 2.8 M, preferably about 0.04 M to about 0.7 M. If ferric hydroxide hydrosol is separately prepared, it is preferred that the hydrosol contain ferric iron at a level of about 0.06 wt. % to about 16.8 wt. %, preferably about 0.11 wt. % to about 3.34 wt. %. If the reaction is carried out using a non-reducing sugar such as sucrose and a basic material such as an alkali metal hydroxide, e.g., the latter may be more highly concentrated since more basic conditions may be necessary to effect a suitable reaction. For example, useful concentrations of an alkali metal hydroxide are about 0.5 wt. % to about 15 wt. %, preferably about 0.7 wt. % to about 10 wt. %.

Useful results are obtained when the molar ratio of (1) the sugar and/or sugar derivative, and (2) the ferric compound, specifically Fe(III) ion in the presence of (OH) ion, is controlled. Generally, the molar ratio of (1):(2) is about 30:1 to about 1:30; in particular, when a sugar derivative is employed, e.g., a gluconate, the molar ratio is about 1:1 to about 1:30, more preferably about 1:2 to about 1:25, based on the gluconate anion. When a non-reducing sugar is employed, e.g., sucrose, the molar ratio of (1):(2) is preferably about 30:1 to about 1:1; more preferably about 25:1 to about 2:1. It has been surprisingly found that where the saccharide is a sugar derivative, the addition of excess sugar derivative, such as a gluconate, or the incorporation of a sugar in excess of the amount of sugar derivative needed to form the iron-saccharidic complex, can moderate or modify, e.g., depress the molecular weight of the iron-saccharidic complex. Such an effect may depend, in part, on the reactant concentrations and/or amounts present when the excess sugar is employed. Generally, such molecular weight depression is not to a level below that which is useful for the iron-saccharidic complex to be useful for parenteral administration. For example, a molecular weight depressing effect has been observed where a sugar such as sucrose is added to a reaction mixture in which sodium gluconate is the saccharide being reacted, such that the amount of sugar is in excess of that required for the molar amount of ferric ion present. Consequently, the use of excess sugar or excess sugar derivative provides an unexpected control tool, or method of moderating the reaction, in order to achieve a desired level of product molecular weight. Furthermore, heating an iron-saccharidic complex produced by the process of the present invention with a saccharide, e.g., a sugar or sugar derivative, can similarly cause a reduction in molecular weight and, consequently, also be used as a means of modifying molecular weight after synthesis of the complex. Generally, a molar excess of at least about 0.01 to about 10,000% can be used for control purposes; alternatively, about 0.1 to about 1,000%; or about 0.2 to about 100%. For example, the use of about 5% to about 25% excess sugar or sugar derivative, can lower the molecular weight of an iron-saccharidic complex by about 50% to about 90% versus what its molecular weight would have been in the absence of such excess sugar.

Formation of the ferric hydroxide, mixing the latter with the saccharide and, if desired, further addition of a base, can be carried out at any convenient temperature, e.g., room temperature or about 20° C. Reaction can be effected at the temperature of mixing the saccharide with the ferric hydroxide and added basic material, provided that the mixing or the temperature of the reaction mixture is greater than about 20° C. However, at temperatures of about 25° C. to about 70° C., extended reaction time may be required in order to obtain the high molecular weight iron-saccharidic complex of the invention in significant yield. If it is desired to increase the reaction rate, the temperature of the reaction mixture is increased to at least about 80° C.; preferably at least about 95° C.; for example, about 100° C. to about 105° C., after achieving the complex assembly point. If the reaction is carried out at ambient pressure, the reaction mass may reach boiling, in which case the heating can be carried out under reflux conditions. Alternatively, the water vapor can be removed or allowed to escape from the system, resulting in a reduction of water and a concentration of the system. If the reaction is carried out under elevated pressure, no boiling may be observed, whereas if it is carried out under reduced pressure, boiling may occur at a lower temperature.

Desirably, the iron-saccharidic complex at high molecular weight is formed in significant yield after a few minutes. Conversely, in the absence of an increase in temperature, particularly if the temperature during ferric hydroxide formation is relatively low, e.g., about 25° C. to about 55° C., a high molecular weight iron-saccharidic complex in appreciable yield can be obtained after extended reaction times. Some amount of iron-saccharidic complex product may be formed almost immediately, e.g., in a few minutes, but it can take much longer to produce significant amounts, e.g., up to about 168 hours; or up to about 72 hours; or up to about 24 hours; in each instance depending on the particular temperature and other reaction conditions. Alternatively, and preferably, heating at an elevated temperature is continued for several minutes, e.g., about 5 minutes, to about 2 hours depending on the temperature; preferably about 8 minutes to about 1 hour; more preferably about 10 minutes to about 30 minutes; for example, about 15 minutes at about 100° C. Useful time/temperature conditions can be readily determined by sampling the reaction mixture and measuring both the yield and molecular weight of the iron-saccharidic complex. Overall, useful product in satisfactory yield can be obtained in a few minutes or as long as about 48 hours. At the conclusion of the reaction, the pH of the mixture is preferably about 8.5 to about 9.5; for example, about 8.7 to about 9.3, but pH need not be independently controlled in order for the desired product to be produced during supplemental heating or following achievement of the complex assembly point.

By following the teachings of the present invention, iron-saccharidic complexes comprising AHS and exhibiting high absolute molecular weights, e.g., typically greater than about 25,000 Daltons and more particularly greater than about 30,000, 50,000, 75,000 or 100,000 Daltons or more. Generally complexes having molecular weights of about 100,000 to about 50,000,000 Daltons can be obtained; for example, molecular weights of about 200,000 to about 2,500,000; about 250,000 to about 1,000,000; or about 275,000 to about 850,000 are readily achieved. As expressed in the present application, molecular weight means weight average molecular weight, Mw; the latter as defined in standard reference texts and, furthermore, as that term is understood by one skilled in the art. See, for example, Encyclopedia of Chemical Technology, $4^{th}$ Ed., Vol. 19, 886-887 (John Wiley & Sons, 1996). Furthermore, unless otherwise explained, the molecular weight values expressed herein are considered "absolute" molecular weights determined as described hereinbelow. The highest useful molecular weight of an iron-saccharidic complex is limited by that which is no longer dispersed in colloidal form in a carrier liquid such as water. In other words, if the molecular weight of the iron-saccharidic complex is so high that it is no longer a useful parenteral product, then one or more of the temperature, pH or other conditions, need to be adjusted in order to reduce the absolute molecular weight of the product. Alternatively, as discussed above, a molecular weight control, or moderating, agent, e.g., excess gluconate or sucrose could be added to the reaction mixture, or to the high molecular weight complex following synthesis, in order to moderate, e.g., depress molecular weight to the desired level. By adjusting the specific reaction conditions described above, iron-saccharidic complexes or AHS compositions having various absolute molecular weights can be targeted, e.g., about 125,000 to about 25,000,000 Daltons; 150,000 to about 10,000,000 Daltons; 175,000 to about 2,500,000 Daltons; as well as other molecular weights within this range, including products having molecular weights similar or equivalent to those commercially available, such as about 289,000 to about 440,000 Daltons, e.g., 417,600 Daltons reported for commercially available sodium ferric gluconate complex. Furthermore, if the absolute weight average molecular weight of a commercial product is found to be different than that reported in the literature or higher at the time of manufacture, e.g., about 500,000 to about 700,000 Daltons, the process of the present invention is sufficiently flexible to allow for synthesis of an iron-saccharidic complex having the correct, desired or appropriate molecular weight. Particularly useful complexes have absolute weight average molecular weights (Mw) of about 350,000 to about 750,000 Daltons; for example, about 500,000 to about 700,000 Daltons.

As noted earlier, the actual molecular weights of the current commercial products are in some dispute. For example, in the Physician's Desk Reference® of 2000, the molecular weight by gel permeation chromatography was reported to be 350,000±23,000 Daltons, providing a range of 327,000 to 373,000 Daltons. Contrast that range with the range recited immediately above, both with reference to the same chemical structural formula.

The process of the present invention can produce AHS based on sodium ferric gluconate having a molecular weight at an average value in either of the ranges recited for the commercial product. Additionally, the product of the present invention can exhibit such molecular weight as synthesized (i.e., with limited separation from the reaction mixture as described below); as synthesized and substantially purified, e.g., as taught in U.S. Pat. No. 6,537,820; as synthesized in the presence of a sugar such as sucrose and with limited or substantial purification; or synthesized in the absence of such a sugar, but with a sugar added post-synthesis. Consequently, a sodium ferric gluconate complex AHS having a molecular weight, in Daltons, of about 25,000 to about 288,000 or to about 441,000 and higher can be produced. For example, in Daltons, about 25,000 to about 285,000 or about 445,000 and higher; about 25,000 to about 275,000 or about 450,000 and higher; etc. In each instance the reference to "and higher" is understood to refer to the upper end of the molecular weight ranges expressed above with regard to the products that can be produced by the process of the present invention. Alternatively, in view of the teachings and flexibility of the present invention, these various synthesis and purification options can be practiced using at least one of the sugars or sugar derivatives described above, other than sodium gluconate, to a molecular weight in the ranges just described or to any of the molecular weight ranges recited above with regard to the present invention, for example, about 25,000 to about 50,000,000 Daltons.

Similarly, the commercial product based on iron(III)-hydroxide in sucrose (ferric hydroxide sucrose complex or FHSC) is described by its manufacturer in the Physician's Desk Reference as having a molecular weight of approximately 34,000-60,000 Daltons and a proposed structural formula as follows: $[Na_2Fe_5O_8(OH).3(H_2O)]n.m(C_{12}H_{22}O_{11})$, where n is the degree of iron polymerization and m is the number of sucrose molecules associated with the iron(III)-hydroxide; there are no stated values for n and m. However, independent measurement of the absolute molecular weight of a sample of this product indicates an absolute weight average molecular weight of 570,000 Daltons. As described above, iron(III)-hydroxide in sucrose can also be synthesized by the process of the present invention so as to match the molecular weight of the commercial product. Additionally, in view of the flexibility and control afforded by the present invention, the process can be used to synthesize FHSC, as well as a hematinic complex based on any of the sugars disclosed above, to any desired molecular weight. In other words, a product corresponding to the commercial product as well as one having a lesser or greater molecular weight. Furthermore, according to the disclosure of U.S. Pat. No. 6,537,820, the commercial FHSC hematinic product was subjected to purification as a consequence of which low molecular weight excipients were removed.

In the process of the present invention, increasing the temperature of the reaction mixture, after the complex assembly point has been achieved, to about 99° C. to about 103° C. can produce an iron saccharidic complex, e.g., a ferric gluconate complex having an absolute molecular weight of about 300,000 to about 700,000 Daltons; a temperature of about 110° C. to about 115° C. can produce a product having an absolute molecular weight of about 28,000,000. In both cases, such products are produced after only a short time at such elevated temperatures, e.g., in about 10 to about 20 minutes; for example, about 15 minutes. The absolute molecular weights identified herein can be determined by the methods described by Beck and Mateer in U.S. Pat. No. 6,537,820, incorporated herein to the extent permitted. Specifically, the non-dextran Fe(III) hematinic of the present invention is a parenterally acceptable species that resembles properties of an association colloid. An association colloid is typically defined, and for the purposes of the present invention, is considered to be a reversible chemical combination due to chemical bonding forces, typically weaker than covalent bonds, wherein up to hundreds of molecules or ions aggregate to form colloidal structures. Consequently, an association colloid will be of a size typical of a colloid, for example, including sizes of from about 1 to about 2000 nanometers or larger; generally about 1 to about 1000 nanometers; more typically, about 1 to about 100 nanometers; for example, about 2 to about 50 nanometers; or about 3 to about 35 nanometers (nm). Although there is no universally accepted definition of a "nanoparticle," they are generally considered to be in the size range of about 1 to about 100 nm or more. Consequently, in view of their size, the iron-saccharidic complexes of the present invention may also be referred to as nanoparticles. Such colloids of ferric ions interacting with saccharidic compounds exhibit directional migration in an electric field in addition to optical activity that can be identified by laser light scattering (LLS). LLS properties relevant herein relate to the Tyndall effect where an incident light beam ($I_o$) passing through a colloid emerges from it at a 90° angle to its original path. Light scattering only occurs if the light interacts with macromolecules such as starches, proteins or other colloidal species where the wavelength of incident light approaches size dimensions of the molecules. Light scattering can occur as destructive interference where the scattered wavelengths interact to cancel each other out or by constructive interference where two wavelengths of light reinforce each other. Mathematical evaluation of LLS data permits size and shape evaluations of various colloidal species. Size, for example, may be estimated in terms of molecular weight for a single molecule or the formula weight for a multi-molecular or ionic aggregate. The weight expressions in either case represent the sum of atomic weights of all atoms present in such structures. Furthermore, the size of light scattering compounds can also be determined using well-known calculation methods in terms of the root mean square radius (RMS radius or Rz value) of the compound, e.g., a colloid or particle, expressed in terms of nanometers (nm). The structural diversity of most aggregates or molecules such as polymers is such that they exist as a frequency distribution of varying weights, typically expressed as an average or mean molecular weight distribution (MWD). Apart from size, colloidal shape can have important implications. For example, if its shape is that of a thin rod, a random coiled structure or a sphere its interaction with other molecules or structures can vary. LLS, including multi-angle laser light scattering (MALLS) or low angle laser light scattering (LALLS), combined with one or more methods of high pressure (or high performance) liquid chromatography (HPLC) integrated detector analysis can be used for evaluating iron-saccharidic complexes. For purposes of the present invention, reference to LLS should be understood to include MALLS, the latter being a preferred type of detector. The use of LLS measurements herein provides a superior and preferred analytical method for characterizing an iron-saccharidic complex that represents the preferred AHS resulting from suitably controlled synthesis. The fundamental mathematical relationships and operation of HPLC in combination with laser light scattering and refractive index detectors for the characterization of macromolecular structures and association colloids has been reported. (see P. Wyatt, Light scattering and absolute characterization of macromolecules, Analytica Chimica Acta. (1993) 272:1-40; incorporated by reference to the extent permitted). In the case of iron saccharidic complexes, such as those of the present invention, the use of high pressure liquid chromatography with MALLS detection measurements is only possible if the "dn/dc" value for such complexes is known or can be determined. The value dn/dc is the ratio of the change in the index of refraction (dn) of an iron-saccharidic complex divided by the corresponding change in its concentration (dc). In order to determine the dn/dc value, an iron-saccharidic complex must first be isolated in a purified form, as taught according to the methods of the '820 patent. This permits determination of a dn/dc value that is characteristic of the therapeutic iron complex. Once the value is determined for a member of a class of such materials, it can be used for other members of the class. In contrast, absent calculation or determination of the dn/dc value of iron complexes purified using the methods of the '820 patent, MALLS characterization and determination of the absolute molecular weights of these products cannot be achieved.

The iron-saccharidic products of the present invention are characterized, in part, by their molecular weight and molecular weight distribution, measured as described above. The values of molecular weight are reported as absolute weight-average molecular weight, Mw. The molecular weight distribution, also referred to as polydispersity, is reported in the standard fashion as the ratio of Mw to Mn, the latter being the absolute number-average molecular weight, also obtained concurrently from the same test method as described above for Mw. Practicing the process of the present invention, useful products can be produced having different molecular weight distributions. The process of the present invention is capable of producing products having a relatively narrow polydispersity. Generally, products having molecular weight distribution in the range of about 1.05 to about 5.0 can be made; typically about 1.08 to about 4.0; preferably about 1.11 to about 3.5; more preferably about 1.14 to about 3.0; most preferably about 1.17 to about 2.5; for example, about 1.20 to about 2.0; alternatively, about 1.20 to about 1.75; or about 1.15 to about 1.60; or about 1.25 to about 1.65. It has been observed that higher Mw iron-saccharidic products produced according to the process of the present invention tend to exhibit higher polydispersity values. However, in some instances, products having significantly high molecular weights and very narrow molecular weight distributions can be produced, e.g., Mw greater than 1,000,000 and a Mw/Mn of about 1.1 to about 1.3; e.g., about 1.2. Such products have been synthesized using a starting material other than sucrose or glucose, e.g., a sugar derivative such as isoascorbic acid. Additionally, particularly desirable iron-saccharidic complexes can be synthesized according to the present invention having an absolute weight average molecular weight, Mw, of about 350,000 to about 750,000 Daltons; especially about 500,000 to about 700,000 Daltons; and a molecular weight distribution, Mw/Mn, of greater than about 1.4 to about 1.6; products of this type based on sodium gluconate have been synthesized.

The product produced by the present invention can be further characterized by various analytical methods including, e.g., light scattering enhanced liquid chromatography; ultraviolet spectroscopy; visible spectroscopy; combined ultraviolet and visible spectroscopy; ultraviolet spectroscopy using photodiode arrays, visible spectroscopy using photodiode arrays and combined ultraviolet and visible spectroscopy using photodiode arrays; infrared spectroscopy, electron spin resonance; pulse polarography; energy dispersive X-ray analysis; circular dichroism and optical rotatory dispersion; fluorescent spectroscopy; polarimetry; pyrolysis mass spectroscopy; nuclear magnetic resonance spectroscopy; differential scanning calorimetry; liquid chromatography-mass spectroscopy; matrix assisted laser desorption/ionization-mass spectrometry; capillary electrophoresis; inductively-coupled plasma spectrometry; atomic absorption; electrochemical analysis; analysis utilizing radioactive isotopes including radioactive iron; antibodies to hematinic substances; retained solids following filtration through a membrane filter having porosity in the range of from about 0.02 to about 0.45 microns; high pressure liquid chromatography coupled with light scattering; and high pressure liquid chromatography coupled with light scattering and including a mass sensitive detector. The product as made and including water can be analyzed, as well as the AHS or iron-saccharidic complex that has been further purified, e.g., in which all or substantially all unreacted components, reaction by-products and low molecular weight species, generally referred to as reaction excipients, have been removed. Additionally, a purified product that is lyophilized to produce a solid, e.g., in powder form, can also be analyzed at the time of production as well as at various times thereafter.

Following synthesis of the high molecular weight iron-saccharidic complex or AHS as described above, the AHS can be recovered or separated from unreacted reagents and/or byproducts of the synthesis process. Routine separation of AHS can be accomplished by precipitation from the reaction mixture using about a 9:1 (volume/volume) ratio of a water miscible diluent with the final reaction mixture wherein AHS was synthesized. The water miscible diluent must have a dielectric constant smaller than that of water such as a $C_1$-$C_4$ linear or branched alcohol or mixtures thereof. The diluent is selected to maintain the parenteral safety of the AHS product if trace amounts are present; a preferred diluent is ethanol. Following precipitation, the AHS can be further purified, such as by filtering, and re-dispersed in a carrier such as water. Further precipitations of the AHS can be implemented to facilitate the cleanup of the AHS product and, depending on the solubility characteristics of the lower molecular weight materials present in the synthesized reaction mixture, such precipitation can result in substantial removal or separation of such lower molecular weight materials. Alternatively, separation of the AHS, as synthesized and contained in the reaction mixture or partially or substantially separated from the reaction mixture post-synthesis, can be accomplished by dialysis, cross-flow dialysis, electrokinetic migration, centrifugation and a process step comprising passing a composition containing the AHS or iron-saccharidic complex through at least one column, also sometimes referred to as a chromatographic column, and separating the column eluate into fractions, at least one of the fractions comprising the desired active hematinic species; such separation techniques are well-known to those skilled in the art. Following the last separation, by, for example, filtration, the AHS can be re-suspended in a suitable fluid carrier; preferably a polar fluid, more preferably water. The AHS product in such a suitable liquid carrier is in the form of colloidal particles, sometimes referred to as a colloidal suspension or colloidal solution. It has the appearance of being clear to the unaided eye because the particles are typically very small, e.g., about 1 to about 50 nanometers, for example, about 10 nanometers in the largest dimension. The composition also typically has a deep reddish-brown color.

Optionally, the AHS produced by the above-described process can be further purified using the methods disclosed in U.S. Pat. No. 6,537,820 ("the '820 patent"). Briefly, the product obtained from the process of the present invention, for convenience referred to as the crude product, preferably before, but optionally after, at least one precipitation and separation, is column fractionated using at least one column to separate unreacted components, reaction by-products and/or low molecular weight excipients, including ferric-carbohydrate compounds having low molecular weights relative to the desired complexes of the present invention, e.g., weight average molecular weight of less than about 3,000 Daltons; or less than about 4,000 Daltons; and also including such materials having weight average molecular weights of less than about 5,000 Daltons or 10,000 Daltons. Alternatively, the crude product can be purified by dialysis in order to separate such excipients.

The resulting purified product can be dried using at least one drying step and it is particularly suitable for lyophilization or freeze-drying by the methods taught in the '820 patent in order to obtain a solid AHS, typically in powder form. Alternatively, the purified product can be spray dried, dried by the application of heat, the application of heat and vacuum or by a combination of the recited drying methods, or drying methods known to those skilled in the art. As described in the '820 patent, the powder is a particularly useful form for long-term storage, e.g., in a sealed foil pouch. For the purposes of the present invention, a "sealed foil pouch" means structures comprising metal films, e.g., aluminum, as well as laminates of plastic and metal composites. When needed, the powder can then be reconstituted by adding an appropriate carrier, e.g., water and other optional or desirable excipient additives for parenteral administration, including, e.g., vitamins, including vitamin B-12, sodium chloride to regulate osmolality, potassium, etc. As noted above, the lyophilized powder can be analyzed by various methods, including infrared, in order to characterize it at the time of production and at intervals thereafter to assess storage stability and product quality. Iron-saccharidic complexes comprising an active hematinic species (AHS) are subject to destabilization and decomposition following their synthesis, particularly if storage conditions are variable and/or unsuitable and when such complexes remain in a diluent or liquid, particularly an aqueous, carrier. In contrast, the dried AHS can be stored for extended periods of time, preferably in a moisture-free environment, including sealed containers. Furthermore, the dried, stable complex can be conveniently transported and reconstituted when needed at the point of use, thereby further extending its stability until just prior to use. For example, the dried AHS can be sealed in moisture-proof containers such as metal foil pouches or glass containers, and stored at ambient temperature (about 20° C. to about 25° C.) or below for extended periods of time. For example, the dried complex can be stored for a period of time ranging from shortly after manufacture, such as from about one week thereafter, as well as for a moderately long storage period of about 6 months, to for as long as about five years or more after manufacture; extended storage can be from about 1 year to about five years, for example, from about 1 year to about 3 years.

Preservation of the dried, preferably lyophilized, AHS product can be maintained in a vacuum or under any inert gas, including, for example, nitrogen, argon and helium (as well as any gas that is not reactive with the lyophilized product) before it is reconstituted for analysis or use. Also, since the lyophilization process alone does not compromise the structure of iron-saccharidic complexes, use of the process has value for maintaining these hematinic agents at various time intervals so as to document the hematinic species present at a given point in time when lyophilization was implemented. This provides a method for archival storage and documenting of product manufacture and quality. Suitably prepared and maintained lyophilized AHS can be safely stored until needed with little risk of significant degradation of the product. Furthermore, the product in such a form can be conveniently shipped to geographically remote locations and conveniently stored until needed, at which time reconstituting the hematinic for parenteral use is readily accomplished. For example, the lyophilized product prepared according to the present invention can be stored in sealed glass or appropriately protected metal containers, preferably topped with a substantially moisture free inert gas. Alternatively, such product can be sealed in a metal foil pouch in a quantity suitable for reconstituting as a single parenteral dose, etc.

The iron-saccharidic complexes of the present invention are usefully prepared so as to produce parenteral hematinic complexes for the delivery of iron to humans. Besides being useful for human treatment, compositions of the invention can be useful for veterinary treatment of companion animals, exotic animals, farm animals, and the like, particularly mammals in need of such treatment. More particularly, compositions of the invention are useful for treatment of hematinically mediated disorders in horses, pigs, dogs and cats. These iron complexes generally occur in a form such that iron can be parenterally and benignly administered to augment hematopoietic mechanisms required for the management of numerous clinical conditions in mammals, particularly in human beings in need thereof. The term "parenteral administration" herein encompasses injection and/or infusion of a composition into or through the skin of a subject, and includes intradermal, subcutaneous, intramuscular, intravenous, intramedullary, intra-articular, intrasynovial, intraspinal, intrathecal and intracardiac administration. Any known device useful for parenteral injection or infusion of drugs can be used to effect such administration.

Useful excipients, i.e., additives, can be intentionally added to the iron-saccharidic complexes of the present invention in order to prepare pharmaceutically useful parenteral compositions. The additives can be in dry form and included with the dried AHS for later reconstitution of a useful dosage comprising most, if not all, of the additives required for parenteral administration, e.g., a unit dosage form. Selection of additives not to include can be based, for example, on consideration of issues relating to storage stability. Alternatively, additives can be mixed with an aqueous preparation of the AHS in order to produce a ready-to-use parenteral composition. Such additives are well-known to those skilled in the art.

A further embodiment of the present invention comprises an article of manufacture comprising a sealed container, pouch, ampoule or vial, preferably a glass vial, having enclosed therewithin a substantially dried or powdered composition, or a liquid composition comprising the AHS, as herein provided in a unit dosage amount and in a sterile condition. In a particular embodiment, such an article of manufacture is provided, prepared by a process as described above. Where the AHS requires reconstitution, the container, e.g., vial, preferably has a capacity sufficient to enable reconstitution of the composition in situ. Generally a capacity of about 1 ml to about 10 ml, preferably about 2 ml to about 5 ml, will be found convenient. The term "vial" herein is used to denote any small container, having a closure, that is suitable for packaging a unit dosage amount of a reconstitutable powder, or an aqueous parenteral composition, preferably in a sterile condition. It will be understood that equivalent forms of packaging, such as an ampoule, a disposable syringe and a syringe cartridge, are encompassed by this embodiment of the invention. Optionally the vial can comprise two compartments, one to contain the reconstitutable powder and one to contain a solvent liquid in an amount sufficient to dissolve the powder. In such a vial the two compartments are interconnected by an aperture wherein a stopper can be engaged to prevent contact of the powder and the solvent liquid until the vial is ready for use. In use, the liquid is brought into contact with the powder by disengagement or puncture of the stopper by any suitable means, for example a device such as a plunger that exerts pressure or drives a needle through the stopper. Examples of such multi-compartment vials include a dual-chamber cartridge for a syringe and a dual-chamber vial such as that available under the trademark Act-O-Vial (Pharmacia Corporation).

Any known parenterally acceptable solvent liquid can be used to reconstitute a powder composition or serve as the diluent or carrier of the iron-saccharidic complex of the invention. Water for injection can be suitable, but will generally provide a hypotonic solution. Accordingly, it is generally preferred to use an aqueous liquid containing a solute such as dextrose or sodium chloride. Illustratively, 0.9% sodium chloride injection USP, bacteriostatic 0.9% sodium chloride injection USP, 5% dextrose injection USP, and 5% dextrose and 0.45% sodium chloride injection USP are suitable. Lactated Ringer's injection USP may also be suitable, as is any diluent, solvent or carrier composition that does not negatively affect the AHS during storage or the period of use. A suitable volume of the solvent or diluent liquid for reconstitution depends on the age and body weight of the subject, the solubility and dosage amount of the therapeutic agent and other factors, readily determined by a skilled professional at the time of administration. Suitable administration amounts are described hereinbelow with regard to currently available hematinic products.

An injectable solution composition prepared by reconstituting a powder composition as herein provided in a parenterally acceptable solvent, preferably an aqueous solvent, is a further embodiment of the present invention. In such a solution composition the therapeutic agent can have limited chemical stability, in which case it is preferred to reconstitute the composition within a short period of time, for example within about one hour, before administration. In other cases the therapeutic agent can exhibit a relatively high degree of chemical stability in solution, and in such cases it is not critical to administer within a short period of time after reconstitution. "Acceptable chemical stability" herein means that the composition, following the defined time period (e.g., about 1 hour, about 30 days, about 6 months or about 2 years), passes a standard test for chemical purity of the therapeutic agent, for example as may be required for approval by a regulatory authority. An example of such a test is the "5% total, 1% single impurity rule", whereby a preparation of a candidate drug must contain not more than 5% total impurities, and not more than 1% of any single impurity.

The buffering agent typically is selected to provide a pH of the composition, upon reconstitution in a physiologically acceptable volume of a parenterally acceptable solvent liquid, that (a) is parenterally acceptable, (b) is consistent with the therapeutic agent being in solution in the solvent liquid, and (c) provides a medium wherein the therapeutic agent exhibits acceptable chemical stability for at least about the time period required for parenteral administration, e.g., one hour following reconstitution. Suitable buffering agents can illustratively be selected from sodium and potassium phosphates, sodium and potassium citrates, mono-, di- and triethanolamines, 2-amino-2-(hydroxymethyl)-1,3-propanediol (tromethamine), etc., and mixtures thereof. Preferred buffering agents are dibasic sodium and potassium phosphates and tromethamine. An especially preferred buffering agent is dibasic sodium phosphate, for example dibasic sodium phosphate anhydrous, heptahydrate, dodecahydrate, etc. The buffering agent is typically the predominant excipient ingredient. In one embodiment of the invention, the substantially dried, reconstitutable AHS-containing composition consists essentially of the therapeutic agent and the buffering agent. Optionally, one or more preservatives can be included in the composition at up to about 0.5% by weight. Suitable illustrative preservatives include methylparaben, propylparaben, phenol and benzyl alcohol.

As discussed above, the process of the present invention can be carried out in a controlled manner to produce high molecular weight iron-compositions over a broad range of molecular weights. Furthermore, the high molecular weight products can be produced without the need to include sucrose or another sugar if, for example, the iron-composition is based on a sugar acid derivative such as sodium gluconate. Consequently, the product produced under such circumstances may be preferred for treating patients with a sensitivity to the presence of additional sugar in the parenteral composition, e.g., diabetic patients. Such products have an advantage in that fewer adverse side-effects can be expected in a patient whose physical well-being may already be compromised beyond the need for parenteral iron. Alternatively, sucrose or another sugar can be added back to the parenteral composition at any desired level suitable for the patient being treated. Such an option was not previously available with prior art products.

Dosage and administration of compositions comprising active hematinic species of the present invention can vary depending on the chemical nature and concentration of the active species and, perhaps, the presence of other components. In solutions for parenteral administration, the iron must be present as ferric iron in a form sufficiently stable to prevent gel formation and precipitation, for example, precipitation of ferric hydrate at physiologically suitable pH. The iron is preferably also present in such a form that no toxic side reactions, whether of a local or of a general type, occur when injecting dosages containing an appropriate and convenient dosage of iron. Solutions of simple salts of iron, e.g., ferric sulfate, cannot be used for parenteral administration because of their relatively high toxicity. Similarly, ferrous iron is not suitable for use in a parenteral iron composition as a consequence of adverse side effects. A typical preparation comprising an iron-saccharidic complex prepared according to the process of the present invention and provided in a suitable container, e.g., an ampoule or vial, generally contains about 5 to 100, e.g., about 7 to about 50, typically about 10 to about 40 mg iron per ml. The specific concentration can be expected to be adjusted depending on whether the composition is intended to be administered by, e.g., injection or intravenously. Furthermore, the composition comprising an iron-saccharidic complex typically further comprises at least one pharmaceutically acceptable adjuvant, diluent and/or carrier. The following descriptions are based on the treatment of human beings, but appropriate treatments for animals are also known or can be determined by a skilled veterinarian based on the specific physical condition, including age, etc., as well as the animal species to be treated. Similarly, a skilled professional can determine the need for, or usefulness of, test dosing prior to administering a particular AHS.

A parenteral iron-saccharidic complex in the form of sodium ferric gluconate can be produced in a composition equivalent to that of a presently available commercial product, for example, in sucrose. Consequently, the composition can be administered in a dosage form and based on an administration schedule equivalent to that currently recommended. The dosage is typically expressed in terms of the milligram (mg) content of elemental iron. For example, the recommended dosage for repletion of iron deficiency in hemodialysis patients is equivalent to 125 mg of iron for a single administration. The product, when provided in the form of a 5 mL ampoule for intravenous injection containing 62.5 mg (12.5 mg/mL) of elemental iron and also containing approximately 20% sucrose w/v (195 mg/mL) in water at a pH of 7.7-9.7, can be administered as a 10 mL dose; equivalent to 125 mg of elemental iron. For slow IV administration (undiluted), 125 mg can be introduced over 10 minutes; for IV infusion (diluted in 0.9% NaCl), 125 mg in 100 mL over 60 minutes. A physician trained in the art can determine the appropriate total dosage needed by a patient based on the medical and physical condition of the patient and the iron improvement required. For example, in order to achieve a favorable hemoglobin or hematocrit response, the current recommendation for the commercial hematinic of the above type is a minimum cumulative dose of 1.0 gram of elemental iron, administered over eight sessions at, e.g., eight sequential dialysis treatment sessions.

Dosage and administration of a parenteral product based on another currently available commercial product in the form of sodium ferric hydroxide in sucrose is also described in the art. Dosage of this form is also typically expressed in terms of elemental iron content. Typically each 5 mL vial of the composition contains 100 mg of elemental iron based on 20 mg/mL. Repletion treatment of iron deficiency in hemodialysis patients is typically 5 mL comprising 100 mg of elemental iron delivered intravenously concurrent with dialysis. Patients typically require a total of 1 gram (1,000 mg) of elemental iron administered in conjunction with 10 sequential dialysis sessions for an appropriate hemoglobin or hematocrit response. Maintenance of appropriate levels of hemoglobin, hematocrit and other laboratory criteria may be determined by a skilled physician, as appropriate.

The products of the present invention include ferric saccharidic complexes having an absolute weight average molecular weight of about 25,000 or more and especially 100,000 Daltons or more and derived from any of the saccharides previously described, including sugars, sugar derivatives and mixtures thereof. Preferred are those that substantially exclude polysaccharides. Furthermore, the products can contain additional saccharide in unmodified form with the proviso that the products of the invention do not correspond precisely to the commercial products identified above as Ferrlecit and Venofer, nor their purified versions as taught in U.S. Pat. No. 6,537,820. Furthermore, the products of the invention are those produced by the process as taught above. In contrast, the currently available commercial products are produced by undefined processes. The net result is that the products of the present invention have an improved excipient profile that, particularly as made, differs from the commercial materials. For example, the iron-saccharidic products herein can be produced under conditions such that undesirable trace metals are avoided or are present at levels substantially lower than currently available commercial products. Additionally, the inventive products herein can be produced in a form free of added sugar, e.g., particularly suitable for a patient having difficulties controlling blood glucose levels, such as a patient with diabetes. Conversely, the products can be produced in a form resulting from purification, as described above, following synthesis and including the controlled addition of a finite level of a sugar or another excipient, e.g., a buffer or a salt, to a defined compositional specification. Overall, the products of the present invention can include and be made to standards that are pharmaceutically equivalent to current commercial products, but having fewer undesirable by-products resulting in improved purity and improved product quality, and, consequently, with potentially improved stability during long term storage. Using the process of the present invention, iron-saccharidic complexes having fewer reaction by-products can be produced. While knowledge of controlling process variables affecting the synthesis, and control such variables, is, of course, important, it has also been found that the nature of the starting saccharide can also affect the quality of the resulting complex product. Specifically, salts of gluconic acid, e.g., sodium gluconate, are particularly preferred, followed by isoascorbic acid, glucose, fructose and sucrose. Furthermore, the addition of a sugar such as sucrose, either during the synthesis or thereafter, can itself result in the formation of undesirable reaction by-products. As discussed above, while application of the technology of U.S. Pat. No. 6,537,820 (R. A. Beck and R. A. Mateer, Jr.) can be effectively used to remove undesirable excipients, the comprehensive disclosure of the present invention is effective in avoiding such by-products in the first instance. Consequently, there are fewer undesirable by-products in the iron-saccharidic complexes of the present invention than in currently available commercial hematinic products.

A process for synthesizing a high molecular weight iron saccharidic complex comprising an active hematinic species is industrially useful. The complex can be further purified, chemically and/or physically modified, e.g., lyophilized, and formulated for storage or administration to humans or animals in parenteral form.

Any range of numbers recited in the specification, or paragraphs hereinafter, describing various aspects of the invention, such as that representing a particular set of properties, units of measure, conditions, physical states or percentages, is intended literally to incorporate expressly herein by reference or otherwise, any number falling within such range, including any subset of numbers or ranges subsumed within any range so recited. Additionally, the term "about" when used as a modifier for, or in conjunction with, a variable, is intended to convey that the values and ranges disclosed herein are flexible and that practice of the present invention by those skilled in the art using, e.g., temperatures, concentrations, pressures, amounts, contents, carbon numbers, properties such as particle size, surface area, solubility, bulk density, etc., that are outside of the stated range or different from a single value, will achieve the desired result, namely, synthesis of a high molecular weight iron saccharidic complex comprising an active hematinic species. For purposes of the present invention, unless otherwise defined with respect to a specific property, characteristic or variable, the term "substantially" as applied to any criteria, such as a property, characteristic or variable, means to meet the stated criteria in such measure such that one skilled in the art would understand that the benefit to be achieved, or the condition or property value desired is met.

EXAMPLES

Example 1

Ferric chloride is reacted or titrated with sodium hydroxide at about 20° C. while the reactants are vigorously stirred to form a ferric hydroxide colloid or hydrosol. While the colloidal ferric hydroxide undergoes continuous stirring, sodium gluconate and sucrose are added. The temperature is raised to about 65° C. and additional sodium hydroxide is added to increase the pH to about 6.0. The molar carbohydrate to Fe(III) concentration ratio is 15:1. The pH of the mixture is further adjusted to a value of about 10.5 and the reaction mixture is heated to about 100° C. A sodium ferric gluconate complex in sucrose is produced.

Example 2

A solution of ferric chloride hexahydrate (0.3699 M) in 0.2 L of water was prepared. While holding the temperature of the ferric chloride solution at about 20° C., sucrose was added to produce a carbohydrate concentration of 0.877 M. After complete dissolution of the sucrose, sodium hydroxide (8.0 M) was added to the reactants with continuous mixing to give a pH of about 11.5. The temperature of the mixture was then raised to about 102° C. and held at that temperature (refluxed) for 120 minutes. The resulting high molecular weight ferric hydroxide sucrose complex had a Mw of 1,570,000 Daltons and a molecular weight distribution or polydispersity, as measured by Mw/Mn, equal to 1.32.

Example 3

200 ml of an aqueous solution of ferric chloride hexahydrate, 0.0555 molar, was added to a 500 ml flask equipped with a stirrer and heating mantel; the pH of the solution was about 1.7. 30 ml of a 0.943 molar aqueous sodium carbonate solution (total of 6.0 g sodium carbonate) was introduced under vigorous stirring and moderate heat was applied, in order to achieve a temperature of about 50° C. The reaction resulted in the formation of colloidal ferric hydroxide and was allowed to continue until $CO_2$ generation ceased; the pH of the resulting ferric hydroxide hydrosol was about 2. While stirring continued, 0.5 g of sodium gluconate was added and incremental amounts of a 3 molar aqueous solution of sodium carbonate were added to the mixture, resulting in the appearance of a milky brown color. Addition of sodium carbonate was continued until the pH increased to about 6.0. The temperature of the reaction mixture was increased to about 100° C. and heating was continued for 15 minutes (total time at elevated temperature was up to 120 minutes), at which time the pH increased to about 9.0. The resulting sodium ferric gluconate complex could be separated from the reaction mixture by precipitation with ethanol. The AHS was re-dispersed in water and tested for absolute molecular weight using HPLC/MALLS and was found to have an absolute molecular weight of about 1,500,000. The AHS is suitable for further purification by dialysis using a membrane suitable for removal of molecular weights less than about 5,000. Samples of the purified AHS composition can be lyophilized (freeze dried) and spray dried using standard conditions suitable for an aqueous composition in order to produce powders comprising the AHS.

Example 4

200 ml of an aqueous solution of ferric chloride hexahydrate, 0.0555 molar, was added to a 500 ml flask equipped with a stirrer and heating mantel. 30 ml of a 0.943 molar aqueous sodium carbonate solution (total of 6.0 g sodium carbonate) was introduced under vigorous stirring and the mixture was maintained at a temperature of about 20° C. The reaction resulted in the formation of colloidal ferric hydroxide and was allowed to continue until $CO_2$ generation ceased; the pH of the resulting ferric hydroxide hydrosol was about 2. While stirring continued, 0.5 g of sodium gluconate was added and the mixture was titrated with incremental amounts of a 3 molar aqueous solution of sodium carbonate. When the pH reached about 3.5 to about 4.0, and each incremental addition of sodium carbonate resulted in the appearance of a deep red color that dissipated with stirring. Further addition of sodium carbonate to a pH of about 6.0 resulted in a milky brown color throughout the mixture that was maintained after stirring. The temperature of the reaction mixture was maintained at about 20° C. and mixing was continued for about 16 hours. At the conclusion of this time period it was found that the pH of the mixture had not increased and no high molecular weight iron-saccharidic complex was formed. In the absence of mixing, a particulate phase separated from the aqueous phase. Heating of the mixture, even to the boiling point, resulted in an orange-brown sludge that was believed to be ferric oxide.

Example 5

200 ml of an aqueous solution of ferric chloride hexahydrate, 0.0555 molar, was added to a 500 ml flask equipped with a stirrer and heating mantel. 30 ml of a 0.943 molar aqueous sodium carbonate solution (total of 6.0 g sodium carbonate) was introduced under vigorous stirring and the mixture was maintained at a temperature of about 20° C. The reaction resulted in the formation of colloidal ferric hydroxide and was allowed to continue until $CO_2$ generation ceased; the pH of the resulting ferric hydroxide hydrosol was about 2. While stirring continues, 0.5 g of sodium gluconate was added and the mixture was titrated with incremental amounts of a 3 molar aqueous solution of sodium carbonate to a final pH of 6.0. During the addition, when the pH reached about 3.5, a milky brown color appeared throughout the mixture that was maintained after stirring and continued titration. The temperature of the reaction mixture was increased to about 52° C. and heating was continued for about 24 hours. After 24 hours the pH was observed to be about 5.5 and the mixture retained a milky appearance, precluding measurement of molecular weight by laser light scattering. A small additional amount of sodium carbonate was added to the mixture, which increased the pH to about 7, at which point the mixture became sufficiently clear to permit a sample of the clear liquid to be tested for molecular weight. The laser light scattering signal indicated that a high molecular weight product was present, e.g., about 2,000,000 Daltons. It appeared that in this example, the reaction conditions (including types and concentrations of reactants, temperature and pH) were near the complex assembly point as a consequence of the initial titration, such that further increasing the pH to about 7 resulted in formation of a small amount of high molecular weight complex. The decline in pH after initial titration is consistent with this observation.

Example 6

200 ml of an aqueous solution of ferric chloride hexahydrate, 0.0555 molar, was added to a 500 ml flask equipped with a stirrer and heating mantel. 30 ml of a 0.943 molar aqueous sodium carbonate solution was introduced under vigorous stirring and the mixture was maintained at a temperature of about 20° C. The reaction resulted in the formation of colloidal ferric hydroxide and was allowed to continue until $CO_2$ generation ceased; the pH of the resulting ferric hydroxide hydrosol was about 2. While stirring continued, 0.5 g of sodium gluconate was added and the mixture was titrated with incremental amounts of a 3 molar aqueous solution of sodium carbonate. When the pH reached about 3.5 to about 4.0, each incremental addition of sodium carbonate resulted in the appearance of a deep red color spot within the milky brown color that dissipated with stirring. Further addition of sodium carbonate to a pH of about 6.0 resulted in a milky brown color throughout the mixture that was maintained after stirring. The temperature of the reaction mixture was increased to about 63° C. and heating was continued for about 16 hours, at which time the pH increased to about 8.2 and the reaction mixture appeared to be clear to the unaided eye and had a deep red color. A significant yield of sodium ferric gluconate complex was obtained having an absolute molecular weight of about 3,300,000 Daltons.

Example 7

200 ml of an aqueous solution of ferric chloride hexahydrate, 0.0555 molar, was added to a 500 ml flask equipped with a stirrer and heating mantel. 30 ml of a 0.943 molar aqueous sodium carbonate solution was introduced under vigorous stirring and the mixture was maintained at a temperature of about 20° C. The reaction resulted in the formation of colloidal ferric hydroxide and was allowed to continue until $CO_2$ generation ceased; the pH of the resulting ferric hydroxide hydrosol was about 2. While stirring continued, about 0.5 g of sodium gluconate was added and the mixture was titrated with incremental amounts of a 3 molar aqueous solution of sodium carbonate. A milky brown color appeared at pH of 3.5 that was maintained after stirring. Further incremental additions of sodium carbonate solution increased the pH to about 9, at which point the mixture appeared to clarify and the color was a deep red or reddish-brown. The temperature of the reaction mixture was increased to about 55° C. and heating was continued for about 16 hours, at which time the pH was about 8.5. Sodium ferric gluconate complex was obtained having an absolute molecular weight of about 3,400,000 Daltons.

Example 8

Ferric chloride hexahydrate (0.0555 M) in 0.2 L of water was reacted with 0.0708 M of sodium carbonate at about 20° C. to a pH of about 6.0 while undergoing vigorous stirring to produce a ferric hydroxide colloid or hydrosol. With continued stirring, 0.0229 M of sodium gluconate was added to the ferric hydroxide hydrosol. The temperature of the reaction mixture was raised to about 102° C. and held at that temperature (refluxed) for 120 minutes. The resulting sodium ferric gluconate complex had a Mw of 3,120,000 Daltons and a Mw/Mn=1.53.

Example 9

Ferric chloride hexahydrate (0.111 M) in 0.2 L of water was reacted with 0.142 M of sodium carbonate at about 20° C. to a pH of about 6.0 while undergoing vigorous stirring to produce a ferric hydroxide colloid or hydrosol. With continuous stirring, 0.092 M of sodium gluconate was added to the ferric hydroxide hydrosol. The temperature of the reaction mixture was raised to about 102° C. and held at that temperature (refluxed) for 120 minutes. The resulting sodium ferric gluconate complex had a Mw of 350,000 and a Mw/Mn=1.21.

Example 10

Ferric chloride hexahydrate (0.111 M) contained in 0.2 L of water was reacted with 0.1415 M sodium carbonate at about 20° C. to a pH of about 6.0 while undergoing vigorous stirring to form a ferric hydroxide colloid or hydrosol. With continuous stirring, 0.0229 M sodium gluconate and then 0.2924 M of sucrose were added to the ferric hydroxide hydrosol. The temperature of the reaction mixture was raised to about 102° C. while undergoing continuous stirring and it was held at that temperature (refluxed) for 120 minutes. The resulting sodium ferric gluconate complex in sucrose had a Mw of 587,000 and a Mw/Mn=1.40.

Example 11

0.18 M of ferric chloride hexahydrate was dissolved in 0.1 L water. A 0.014 M amount of sodium carbonate was added to the ferric chloride solution and stirred until release of $CO_2$ ceased. 0.0039 M of isoascorbic acid (erythorbic acid) was added to the solution and the pH was then adjusted to pH 11.0 with 4.44 M sodium hydroxide whereupon the reagent mixture was refluxed for 90 minutes, resulting in a ferric-saccharidic complex having an absolute weight average molecular weight of 1,750,000 Daltons (Rz=35.3), and a polydispersity, Mw/Mn, of 1.22.

Example 12

Five separate synthesis reactions identified as A, B, C, D and E were prepared using 0.1 L of 0.356 M ferric chloride hexahydrate. Glucose was added to reaction mixtures A, B, C, D and E to provide molar concentrations of 0.555, 0.4127, 0.3667, 0.2778 and 0.2222 M, respectively. The addition of 0.0625 M sodium hydroxide and 0.029 M sodium carbonate to each 0.1 L reaction mixture resulted in a pH of about 10.0 during a minute reflux period. Table 2 shows absolute molecular weights for iron complexes produced and their relationship to the starting molar concentration of carbohydrate (for convenience, ferric chloride hexahydrate is referred to in the table as ferric chloride).

TABLE 1

| Expt. | Ferric chloride, M | Glucose, M | Molecular Weight, Daltons | Polydispersity, Mw/Mn | Rz, nm |
|---|---|---|---|---|---|
| A | 0.3566 | 0.555 | 3,000,000 | 2.54 | 24 |
| B | 0.3566 | 0.4127 | 609,000 | 1.36 | 12 |
| C | 0.3566 | 0.3667 | 597,000 | 1.48 | 9.7 |
| D | 0.3566 | 0.2778 | 389,000 | 1.74 | 16 |
| E | 0.3566 | 0.2222 | 3,600,000 | 3.24 | 33 |

Example 13

A 0.18 M ferric chloride hexahydrate reactant solution was prepared using 0.1 L of water. Glucose was added to the ferric chloride hexahydrate solution with mixing to give a carbohydrate concentration of 0.18 M. This was followed by addition of sodium hydroxide (0.0625 M) and sodium carbonate (0.0145 M). The reaction mixture maintained a pH of about 10.5 during a 90 minute reflux period at about 102° C. This reaction mixture was designed to be about one-half the reagent concentration of Example 12(C) while holding the reaction volume constant at 0.1 L. The product of Example 12(C) was characterized by an absolute molecular weight of 597,000 (Rz=9.7) and a polydispersity, Mw/Mn=1.48, whereas the corresponding product of this experiment had an absolute weight of 299,000 (Rz=9.4) and a polydispersity, Mw/Mn=1.21.

Example 14

Four reactions were conducted, identified as A, B, C and D, using 0.222 M ferric chloride hexahydrate dissolved in a 0.2 L aqueous volume in a 0.5 L flask. The mixture was continuously stirred and sodium carbonate was added to each reaction mixture to give a 0.283 M concentration. The only variable for each reaction mixture was the molar concentration of sodium gluconate where "A" had a concentration of 0.0573 M; "B" was 0.05157 M; "C" was 0.05038 M; and "D" was 0.04584 M. The individual reaction mixtures were titrated using 3.0 M sodium carbonate to give a pH of 6.2 prior to boiling at 102° C. for 90 minutes. The reaction products were characterized using HPLC with in-line MALLS detection that resulted in absolute molecular weights as follows: A=303,000 and Mw/Mn=1.41; B=597,000 and Mw/Mn=1.54; C=1,627,000 and Mw/Mn=2.00; and D=2,104,000 and Mw/Mn=2.03. The results of this experiment indicate that the absolute molecular weight for the active hematinic species (AHS) produced was related to the amount of sodium gluconate reacted with ferric chloride at constant reaction volume.

Example 15

Two separate reactions were conducted in which 0.0444 M ferric chloride hexahydrate was added to 0.15 L of water in a 0.5 L flask equipped with a magnetic stirrer and heating mantel. 40 mL of 1.41 M sodium carbonate was added to bring each reaction mixture volume to 0.19 L whereupon 10 mL of 1.032 M sodium gluconate was added to bring each total reaction volume to 0.20 L. Each reaction mixture was titrated to about pH 6.2 using 3.0 M sodium carbonate with continuous mixing. The temperature was held at about 20° C. One reaction mixture was identified as "A" and the other "B". Reaction mixture "A' was brought to boiling and refluxed at about 102° C. for 90 minutes. Reaction mixture "B" was similarly refluxed after 20% by weight sucrose was added to the reaction mixture. The product from reaction "A" had an absolute weight average molecular weight of 597,000 Daltons and Mw/Mn=1.54, while that from reaction "B" had an absolute weight average molecular weight of 163,000 Daltons and Mw/Mn=1.18.

Example 16

Iron complex synthesis was studied using fixed molar ratios of both iron-to-carbonate and iron-to-gluconate reactants while their molar masses all increased in a fixed reaction volume of 0.2 L. Table 2 defines the test matrix for three experiments denoted as A, B and C. The ferric chloride hexahydrate was dissolved in a 0.2 L aqueous volume by mixing with a magnetic stirrer whereupon sodium carbonate was added. The mixture was allowed to clarify for 20 minutes before sodium gluconate was added. A 3.0 M solution of sodium carbonate was added drop-wise to achieve a 6.2 pH. The reaction mixture was then boiled for 90 minutes and analyzed using HPLC with MALLS detection. Results are shown in Table 2.

TABLE 2

| Component | Experiment A | Experiment B | Experiment C |
|---|---|---|---|
| Ferric chloride hexahydrate (FCH), M | 0.111 | 0.166 | 0.222 |
| Sodium carbonate, M | 0.142 | 0.2123 | 0.283 |
| Molar ratio: FCH/sodium carbonate | 0.782 | 0.782 | 0.784 |
| Sodium gluconate, M | 0.02293 | 0.0344 | 0.04587 |
| Molar ratio: FCH/sodium gluconate | 4.84 | 4.83 | 4.84 |
| Absolute molecular weight | 1,390,000 | 635,000 | 2,104,000 |
| Polydispersity, Mw/Mn | 1.81 | 1.48 | 2.10 |
| Rz, nm | 18.5 | 18.0 | 23.7 |

Example 17

0.22 M ferric chloride hexahydrate was dissolved 0.1 L of water. Sodium carbonate was then added to give a 0.28 M concentration. When the evolution of $CO_2$ ceased, 0.0166 M sodium gluconate was added to the reagent mixture. The pH of the reaction mixture was then adjusted to 6.5 using 4.25 M sodium hydroxide. The reaction developed a pH of about 10.5 during a 30-minute reflux at about 102° C. The product had an absolute weight average molecular weight of 72,000 Daltons (Rz=28.8) and a polydispersity, Mw/Mn, of 1.42).

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

What is claimed is:

1. A process for the preparation of a high molecular weight iron-saccharidic complex, said complex suitable for parenteral administration in human or veterinary medicine, comprising:
    (1) providing a reaction mixture at reaction conditions, said reaction mixture having a pH and formed from:
        (i) water;
        (ii) at least one compound selected from the group consisting of glucose, sodium gluconate and sucrose;
        (iii) at least one ferric salt selected from the group consisting of ferric chloride, ferric nitrate, ferric acetate, ferric sulfate, and double ferric salts; and
        (iv) a basic reactant selected from the group consisting of alkali metal hydroxides, ammonium hydroxide, alkaline earth metal hydroxides, carbonates of alkali metals and mixtures thereof;
    wherein said reaction conditions include:
        (a) a molar ratio of compound (ii) to ferric salt (iii) of about 30:1 to about 1:30; and
        (b) the reaction mixture is at a first temperature of about 20° C. up to 85° C.;
    (2) modifying said reaction conditions to the extent required in order to obtain at least the following pH and temperature by:
        (x) adding a base selected from the group consisting of alkali metal hydroxides, ammonium hydroxide, alkaline earth metal hydroxides, carbonates of alkali metals and mixtures thereof, the same or different as in (1)(iv) above, in an amount effective to increase the pH of said reaction mixture to at least 5.0; and
        (y) heating said reaction mixture to a second temperature and for a time, said second temperature greater than said first temperature and at least 40° C.;
    provided said reaction conditions as modified are sufficient for the reaction mixture to reach a final pH of at least 7.0 and to form said iron-saccharidic complex having an absolute weight average molecular weight of about 25,000 Daltons or more.

2. The process of claim 1 wherein said compound (1)(ii) is sodium gluconate and said molar ratio is about 1:1 to about 1:30.

3. The process of claim 1 wherein said ferric compound is ferric chloride and said basic reactant in step (iv) is sodium hydroxide.

4. The process of claim 1 wherein said base in step (2)(x) is selected from the group consisting of alkali metal hydroxides, alkaline earth metal hydroxides, carbonates of alkali metals and mixtures thereof.

5. The process of claim 1 wherein the pH in step (2) is 5.0 to about 12.0.

6. The process of claim 1 wherein the temperature is elevated in step (y) to between greater than 85° C. to about 115° C.

7. The process of claim 1 wherein the temperature is elevated in step (y) to result in reflux conditions.

8. The process of claim 1 wherein said iron-saccharidic complex has an absolute weight average molecular weight, in Daltons, of between about 25,000 to about 5,000,000.

9. The process of claim 1 wherein said at least one compound is selected from the group consisting of sodium gluconate, sucrose and a mixture of sodium gluconate and sucrose, the reaction product of said ferric salt and basic reactant of step (1) is an aqueous ferric hydroxide composition in colloidal form and the base in step (2)(x) is sodium carbonate or sodium hydroxide.

10. The process of claim 1, further comprising the step, (3) of substantially separating said high molecular weight iron-saccharidic complex from said reaction mixture.

11. The process of claim 10, further comprising the step of drying said substantially separated iron-saccharidic complex.

12. A process for the preparation of a high molecular weight iron-saccharidic complex, said complex suitable for parenteral administration in human or veterinary medicine, comprising:
- (1) providing a reaction mixture at reaction conditions, said reaction mixture having a pH, and formed from:
  - (i) water;
  - (ii) at least one ferric salt selected from the group consisting of ferric chloride, ferric nitrate, ferric acetate, ferric sulfate, double ferric salts and mixtures thereof; and
  - (iii) a basic reactant to convert substantially all of the ferric salt to ferric hydroxide;
- to which is added;
- (2) at least one compound selected from the group consisting of glucose, sodium gluconate and sucrose;
- wherein said reaction conditions include:
  - (a) a molar ratio of the compound (2) to ferric salt (ii) is about 30:1 to about 1:30;
  - (b) the reaction mixture is at a first temperature of about 20° C. up to 85° C.;
- (3) modifying said reaction conditions to the extent required in order to obtain at least the following pH and temperature by:
  - (x) adding a base, the same or different as in (1)(iii) in an amount effective to increase the pH of said reaction mixture to at least 5.0; and
  - (y) heating said reaction mixture to a second temperature and for a time, said second temperature greater than said first temperature and at least 40° C.;

provided said reaction conditions as modified are sufficient for the reaction mixture to reach a final pH of at least 7.0 and to form said iron-saccharidic complex having an absolute weight average molecular weight of about 25,000 Daltons or more.

13. The process of claim 12 wherein said ferric compound is ferric chloride and said basic reactant in (1)(iii) is sodium hydroxide.

14. The process of claim 12 wherein said compound (2) is sodium gluconate and said molar ratio is about 1:1 to about 1:30.

15. The process of claim 12 wherein said base in step (3)(x) is selected from the group consisting of alkali metal hydroxides, alkaline earth metal hydroxides, carbonates of alkali metals and mixtures thereof.

16. The process of claim 12 wherein the pH is raised in step (3)(x) to between 5.0 to about 12.0.

17. The process of claim 12 wherein the temperature is elevated in step (3)(y) to between greater than 85° C. to about 115° C.

18. The process of claim 12 wherein the temperature is elevated in step (3)(y) to result in reflux conditions.

19. The process of claim 12 wherein said iron-saccharidic complex has an absolute weight average molecular weight, in Daltons, of between about 25,000 to about 5,000,000.

20. The process of claim 12 wherein said at least one compound in (2) is selected from the group consisting of sodium gluconate, sucrose and a mixture of sodium gluconate and sucrose, and the base in step (3)(x) is sodium carbonate or sodium hydroxide.

21. The process of claim 12, further comprising the step (4) of substantially separating said high molecular weight iron-saccharidic complex from said reaction mixture.

22. The process of claim 21 further comprising the step of drying said substantially separated iron-saccharidic complex.

* * * * *